US006933108B2

(12) United States Patent
Goldsmith et al.

(10) Patent No.: US 6,933,108 B2
(45) Date of Patent: Aug. 23, 2005

(54) METHODS AND COMPOSITIONS FOR USE IN THE TREATMENT OF FILOVIRUS MEDIATED DISEASE CONDITIONS

(75) Inventors: Mark A. Goldsmith, San Francisco, CA (US); Stephen Chan, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 495 days.

(21) Appl. No.: 09/733,395

(22) Filed: Dec. 8, 2000

(65) Prior Publication Data

US 2003/0082517 A1 May 1, 2003

Related U.S. Application Data

(60) Provisional application No. 60/170,004, filed on Dec. 9, 1999, and provisional application No. 60/237,421, filed on Oct. 2, 2000.

(51) Int. Cl.[7] .......................... C12Q 1/70; C12Q 1/68; C12P 21/00; C12P 19/34
(52) U.S. Cl. .................. 435/5; 435/6; 435/69.1; 435/320.1; 435/7.21; 435/91.2; 435/235.1; 536/23.1; 536/23.4; 530/300; 530/350
(58) Field of Search .................... 435/5, 6, 69.1, 435/320.1, 7.21, 91.2, 235.1; 536/23.1, 23.4; 530/300, 350

(56) References Cited

U.S. PATENT DOCUMENTS

| 5,416,016 A | 5/1995 | Low et al. ............... 435/240.1 |
| 5,447,851 A | 9/1995 | Beutler et al. ............. 435/69.7 |
| 5,837,533 A | 11/1998 | Boutin ..................... 435/320.1 |
| 6,093,382 A | 7/2000 | Wedeking et al. ......... 424/1.65 |
| 6,589,730 B1 * | 7/2003 | Larocca et al. ................ 435/5 |

OTHER PUBLICATIONS

Chan et al. (2000) "Distinct Mechanisms of Entry by Envelope Glycoproteins of Marburg and Ebola (Zaire) Viruses." *Journal of Virology*, vol. 74(10):4933–4937.

Elwood et al. (1997) "The Divergent 5' Termini of the α Human Folate Receptor (hFR) mRNAs Originate from Two Tissue–Specific Promoters and Alternative Splicing: Characterization of the α hFR Gene Structure." *Biochemistry*, vol. 36:1467–1478.

Genbank Accession No. U31033, deposited Apr. 12, 1996.

Genbank Accession No. NC_002549, deposited Feb. 10, 1999.

Genbank Accession No. NC_001608, deposited Jun. 9, 2000.

Genbank Accession No. NM_016731, deposited Nov. 2, 2000.

Roberts et al. (1997) "Tissue–specific promoters of the α human folate receptor gene yield transcripts with divergent 5' leader sequences and different translational efficiencies." *Biochem. J.*, vol. 326(Pt. 2):439–447.

Roberts et al. (1998) "Role of Individual N–Linked Glycosylation Sites in the Function and Intracellular Transport of the Human α Folate Receptor." *Archives of Biochemistry and Biophysics*, vol. 351(2):227–235.

Sadasivan et al. (1989) "The Complete Amino Acid Sequence of a Human Folate Binding Protein from KB Cells Determined from the cDNA." *The Journal of Biological Chemistry*, vol. 264(10):5806–11.

Xu et al. (1998) "Immunization for Ebola virus infection." *Nature Medicine*, vol. 4(1):37–42.

* cited by examiner

*Primary Examiner*—Michael Pak
*Assistant Examiner*—Nirmal Basi
(74) *Attorney, Agent, or Firm*—Paula A. Borden; Bret E. Field; Bozicevic, Field & Francis, LLP

(57) ABSTRACT

Methods and compositions are provided for at least slowing the progression of a filovirus mediated disease condition in a host. In the subject methods, an effective amount of an agent that at least reduces the amount of folate receptor mediated filovirus cell entry is administered to the host. The subject methods find use in both the prevention and treatment of filovirus associated disease conditions, including Marburg and Ebola-Zaire virus mediated disease conditions.

7 Claims, 15 Drawing Sheets

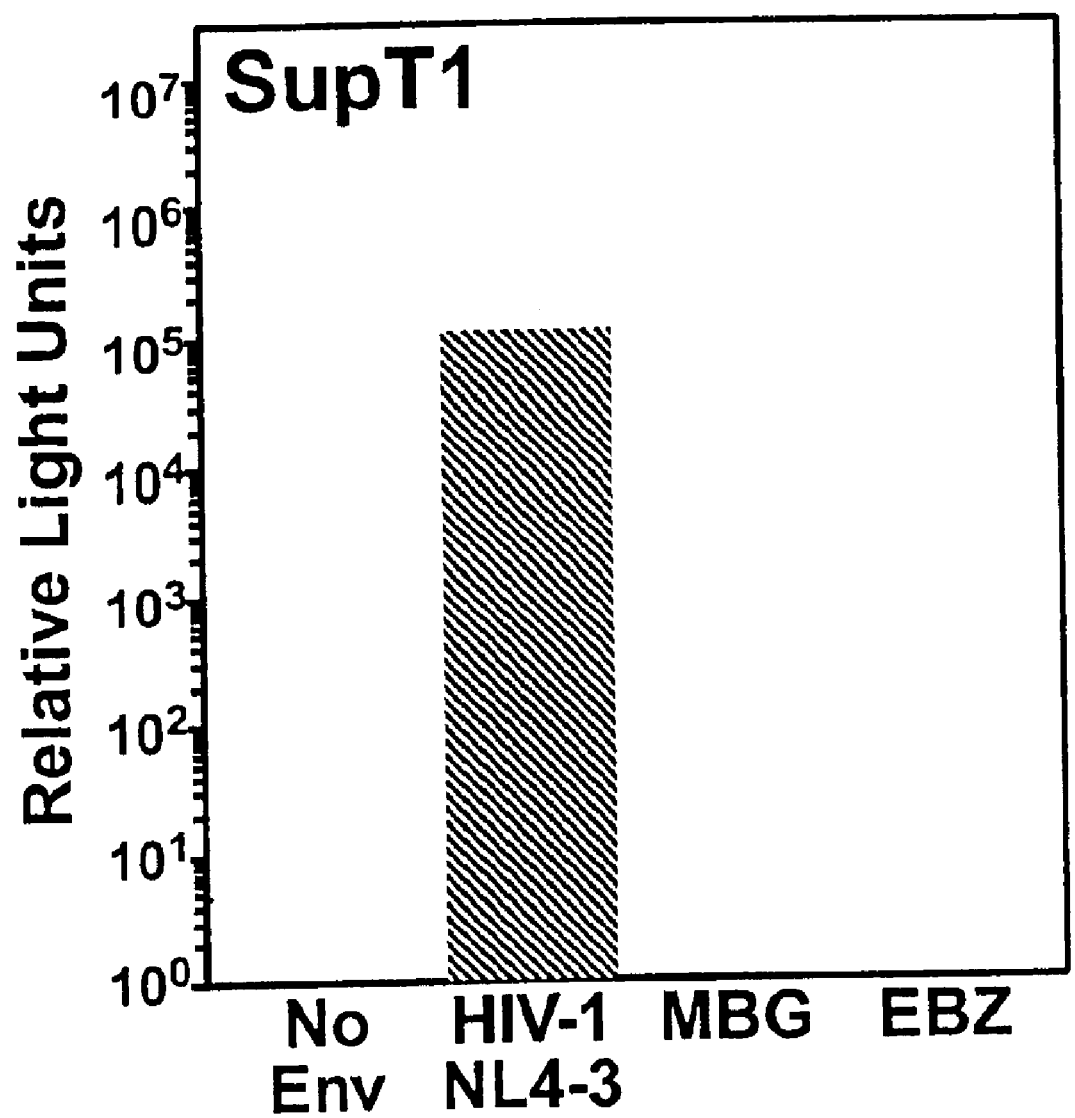

FIGURE 2B

Efficiency of Infection in Jurkat-EctR Cells of Retroviral cDNA Library

FIGURE 4

Specific Survival of Jurkat-EctR Cells Transduced with an Expression Library and Challenged with MBG-Blasti Pseudotype Virus

| | Cells/ml after Selection | |
|---|---|---|
| | Trypan Blue Positive | Trypan Blue Negative |
| Jurkat-EctR Controls | | |
| No virus challenge | > 20,000 | 0 |
| MBG-blasti challenge | > 20,000 | 0 |
| VSV-blasti challenge | 95,200 | 60,000 |
| Jurkat-EctR (+ HeLa library) after MBG-blasti challenge | | |
| Batch 2-11 | > 20,000 | 1,800 |
| Batch 2-14 | > 20,000 | 3,200 |
| Batch 2-23 | > 20,000 | 1,400 |
| Batch 2-24 | > 20,000 | 1,600 |

FIGURE 5

Figure 5: Rechallenge of Jurkat EctR Batches Selected in Blasticidin S with VSV, Ebola-Zaire, and Marburg Luciferase Pseudotype Viruses

FIGURE 6

Transient Transfection of Jurkat Cells
Reveals Reconstitution of Permissivity for Entry
by Marburg Luciferase Pseudotypes

FIGURE 7

Inhibition of Infection by Marburg and Ebola-Zaire Pseudotype Viruses after Phospholipase C treatment of Target Cells

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: synthetic sequence

<400> SEQUENCE: 1
gcgcgaaata ctcactcgag g                                             21

<210> SEQ ID NO 2
<211> LENGTH: 22
<212> TYPE: DNA
<213> ORGANISM: Artificial Sequence
<220> FEATURE:
<223> OTHER INFORMATION: synthetic sequence

<400> SEQUENCE: 2
tatagcccta ccactagagt cc                                            22
```

METHODS AND COMPOSITIONS FOR USE IN THE TREATMENT OF FILOVIRUS MEDIATED DISEASE CONDITIONS

CROSS REFERENCE TO RELATED APPLICATIONS

This application claims priority under 35 U.S.C. §119(e) to provisional patent applications Ser. Nos. 60/170,004, filed Dec. 9, 1999 and 60/237,421, filed Oct. 2, 2000, each of which is incorporated herein by reference in its entirety.

FIELD OF THE INVENTION

The field of this invention is virology, and in particular filoviruses.

BACKGROUND OF THE INVENTION

Filoviruses belong to a virus family called Filoviridae and can cause severe hemorrhagic fever in humans and non-human primates. So far, only two members of this virus family have been identified: Marburg virus and Ebola virus. Four subtypes of Ebola virus have been identified: Ivory Coast, Sudan, Zaire, and Reston. The Reston subtype is the only known filovirus that does not cause severe disease in humans; however, it can be fatal in monkeys.

Filoviruses, including the Marburg and Ebola viruses, cause sporadic epidemics of human disease characterized by systemic hemorrhage, multi-organ failure and death in most instances. In an outbreak or isolated case among humans, just how the virus is transmitted from the natural reservoir to a human is unknown. Once a human is infected, however, person-to-person transmission is the means by which further infections occur. Specifically, transmission involves close personal contact between an infected individual or their body fluids, and another person. During recorded outbreaks of hemorrhagic fever caused by filovirus infection, persons who cared for or worked very closely with infected individuals were especially at risk of becoming infected themselves. Nosocomial transmission through contact with infected body fluids, e.g., via re-use of unsterilized syringes, needles, or other medical equipment contaminated with these fluids—has also been an important factor in the spread of disease. When close contact between uninfected and infected persons is minimized, the number of new filovirus infections in humans usually declines. Although in the laboratory the viruses display some capability of infection through small-particle aerosols, airborne spread among humans has not been clearly demonstrated.

The onset of illness is abrupt, and initial symptoms resemble those of an influenza-like syndrome. Fever, headache, general malaise, myalgia, joint pain, and sore throat are commonly followed by diarrhea and abdominal pain. A transient morbilliform skin rash, which subsequently desquamates, often appears at the end of the first week of illness. Other physical findings include pharyngitis, which is frequently exudative, and occasionally conjunctivitis, jaundice, and edema. After the third day of illness, hemorrhagic manifestations are common and include petechiae as well as frank bleeding, which can arise from any part of the gastrointestinal tract and from multiple other sites.

There is currently no accepted vaccine or direct therapy for the clinical manifestations of infection, other than general supportive measures. Interferon and ribavirin show no in vitro effect against these agents. The case-fatality rate has been estimated to range from 30% to 80%.

In view of the foregoing discussion, there is a need for the development of vaccine and/or treatment protocols for these types of disease conditions. The present invention addresses this need.

Representative Literature

Xu et al. (1998) *Nat. Med.* 4:37–42.

SUMMARY OF THE INVENTION

Methods and compositions are provided for at least slowing the progression of a filovirus mediated disease condition in a host. In the subject methods, an effective amount of an agent that at least reduces the amount of folate receptor mediated filovirus cell entry is administered to the host. The subject methods find use in both the prevention and treatment of filovirus associated disease conditions, including Marburg and Ebola-Zaire virus mediated disease conditions.

The invention further provides agents useful in treating a filovirus-mediated disease condition, as well as compositions comprising the agents. Agents include those that inhibit filovirus binding to a folate receptor on the cell surface, agents that reduce the level of folate receptor on the cell surface, and agents that modulate the folate receptor such that binding of a filovirus to the folate receptor is reduced.

The invention further provides screening methods for identifying agents that reduce filovirus entry into a susceptible cell. Both cell-free and cell-based assay methods are provided.

BRIEF DESCRIPTION OF THE DRAWINGS

FIGS. 1A to 1C provide graphical results showing that co-expression of an envelope negative HIV clone with a gene encoding Marburg or Ebola Zaire envelope glycoproteins leads to the generation of infectious virion particles with properties of the parental filovirus.

FIGS. 2A and 2B provide a graphical representation of the results of a permissivity screening assay.

FIG. 4 provides a table of the results of viability assay in which Jurkat EctR cells were challenged with a retroviral cDNA library and HIV blasti-pseudotype viruses after selection in 40 $\mu$g/ml blasticidin S.

FIG. 5 provides graphical results from an assay in which Jurkat EctR batches selected for blasticidin S were rechallenged with VSV, Ebola-Zaire and Marburg luciferase pseudotype viruses.

FIG. 6 provides the graphical results of an assay in which the infection of Jurkat EctR cells transiently expressing truncated human folate receptor alpha with a Marburg pseudotype virus was studied.

FIG. 7 provides a graphical representation of an assay in which the infection of target cells by Marburg and Ebola-Zaire pseudotype viruses after phospholipase C treatment was studied.

FIGS. 13A–D provide the graphical results of assays showing that expression of FR-α in Jurkat-EctR cells reconstitutes permissivity to entry mediated by either MBG or EBO-Z GP. FIG. 13A shows that pre-treatment of HeLa cells with phospholipase C resulted in complete abrogation of entry by EBO-Z luciferase virus. FIG. 13B shows that the reconstituted Jurkat-EctR cell clone A7-1, selected after challenge by EBO-Z-blasti virus and transduced with a cDNA encoding FR-α, is infectable by both MBG and EBO-Z luciferase viruses, unlike Jurkat-EctR parental cells. FIG. 13C shows that Jurkat-EctR F10 cells reconstituted for infection by MBG-blasti virus and transduced with a cDNA encoding a truncated FR-α, are infectable by both MBG and EBO-Z luciferase viruses, unlike Jurkat-EctR parental cells. FIG. 13D shows that entry by EBO-Z luciferase virus into Jurkat-EctR F10 cells is specifically abrogated in the presence of monoclonal mouse anti-FR IgG1 compared with levels observed with isotype anti-p24 IgG1.

FIGS. 14A–C provide the graphical results of assays showing that inhibition of virion access to FR-α inhibits entry of EBO-Z luciferase virus in naturally infectable HOS and Vero E6 cells. FIG. 14A shows that entry by EBO-Z, but not Ampho, luciferase virus into HOS cells is specifically inhibited by extracellular folic acid. FIG. 14B shows that infection of HOS cells by EBO-Z, but not VSV, luciferase virus specifically decreases in the presence of soluble bovine FBP. FIG. 14C shows that entry by EBO-Z, but not VSV, luciferase virus into Vero E6 cells is completely abrogated in the presence of polyclonal rabbit anti-bovine FBP, compared with levels observed in normal rabbit sera.

DEFINITIONS

By "subject" or "individual" or "host" or "patient," which terms are used interchangeably herein, is meant any subject, particularly a mammalian subject, for whom diagnosis or therapy is desired, particularly humans. Other subjects may include non-human primates, cattle, dogs, cats, guinea pigs, rabbits, rats, mice, horses, and so on.

As used herein, the term "a filovirus-mediated disease condition" encompasses a condition which is a direct result of filovirus infection; and a condition which is an indirect result, e.g., a sequela, of a filovirus infection. Such conditions include, but are not limited to, fever, internal hemorrhaging, edema, organ failure, headache, malaise, myalgia, nausea, vomiting, bleeding of needle puncture sites, hematemesis, melena, petechiae, ecchymosis, maculopapular rash, disseminated intravascular coagulation, shock, jaundice, conjunctivitis, diarrhea, pharyngitis, convulsions, delirium, coma, oligura, and epistaxis.

As used herein, "an immune response" is meant to encompass cellular and/or humoral immune responses that are sufficient to inhibit or prevent infection, or prevent or inhibit onset of disease symptoms caused by a filovirus, and to reduce the likelihood of an infection by a filovirus.

The terms "peptide," "oligopeptide," "polypeptide," "polyprotein," and "protein", are used interchangeably herein, and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at http://ww.ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. See *J. Mol. Biol.* 48: 443–453 (1970).

Of interest is the BestFit program using the local homology algorithm of Smith Waterman (Advances in Applied Mathematics 2: 482–489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127–149, 1988, Alan R. Liss, Inc. Percent sequence identity is calculated by FastDB based upon the following parameters:

| | |
|---|---|
| Mismatch Penalty: | 1.00; |
| Gap Penalty: | 1.00; |
| Gap Size Penalty: | 0.33; and |
| Joining Penalty: | 30.0. |

One parameter for determining percent sequence identity is the "percentage of the alignment region length" where the strongest alignment is found.

The percentage of the alignment region length is calculated by counting the number of residues of the individual sequence found in the region of strongest alignment. This number is divided by the total residue length of the target or query polynucleotide sequence to find a percentage. An example is shown below:

Figure 1A:
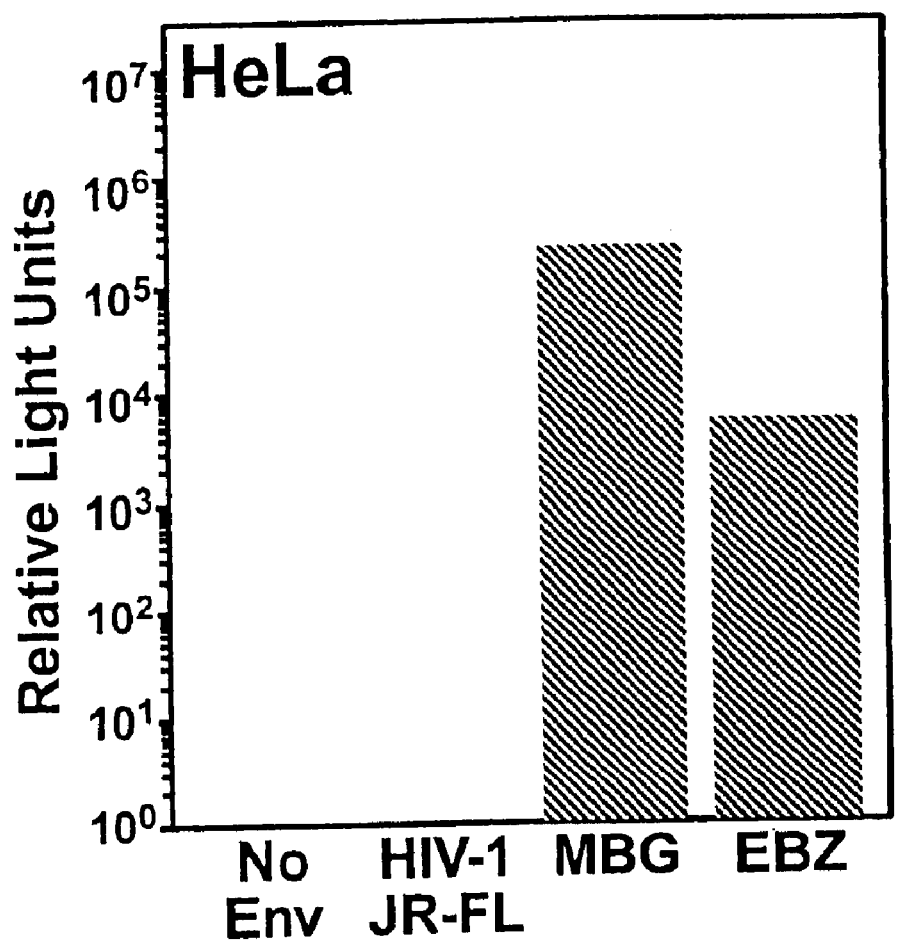

Target sequence:    GCGCGAAATACTCACTCGAGG         SEQ ID NO:01)
                        |   |||  ||||  |||
Query sequence      TATAGCCCTAC.CACTAGAGTCC
                    1       5       10      15    (SEQ ID NO:02)

The region of alignment begins at residue 9 and ends at residue 19. The total length of the target sequence is 20 residues. The percent of the alignment region length is 11 divided by 20 or 55%, for example.

Percent sequence identity is calculated by counting the number of residue matches between the target and query polynucleotide sequence and dividing total number of matches by the number of residues of the target or query sequence found in the region of strongest alignment. For the example above, the percent identity would be 10 matches divided by 11 residues, or approximately, 90.9%

The percent of the alignment region length is typically at least about 55% of total length of the sequence, more typically at least about 58%, and even more typically at least about 60% of the total residue length of the sequence. Usually, percent length of the alignment region can be as great as about 62%, more usually as great as about 64% and even more usually as great as about 66%.

The terms "antigen" and "epitope" are well understood in the art and refer to the portion of a macromolecule which is specifically recognized by a component of the immune system, e.g., an antibody or a T-cell antigen receptor. Epitopes are recognized by antibodies in solution, e.g., free from other molecules. Epitopes are recognized by T-cell antigen receptor when the epitope is associated with a class I or class II major histocompatibility complex molecule.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a FRα polypeptide.

The term "binds specifically," in the context of antibody binding, refers to high avidity and/or high affinity binding of an antibody to a specific polypeptide i.e., epitope of an FR polypeptide. Antibody binding to an epitope on a specific FR polypeptide (also referred to herein as "an FR epitope") is preferably stronger than binding of the same antibody to any other epitope, particularly those which may be present in molecules in association with, or in the same sample, as the specific polypeptide of interest, e.g., binds more strongly to a specific FR epitope than to a different FR epitope so that by adjusting binding conditions the antibody binds almost exclusively to the specific FR epitope and not to any other FR epitope, and not to any other FR polypeptide which does not comprise the epitope. Antibodies which bind specifically to an FR polypeptide may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to a specific FR polypeptide with a binding affinity of $10^7$ mole/l or more, preferably $10^8$ mole/liters or more are said to bind specifically to the specific FR polypeptide. In general, an antibody with a binding affinity of $10^6$ mole/liters or less is not useful in that it will not bind an antigen at a detectable level using conventional methodology currently used.

By "antisense polynucleotide" is meant a polynucleotide having a nucleotide sequence complementary to a given polynucleotide sequence (e.g, a polynucleotide sequence encoding a FR polypeptide) including polynucleotide sequences associated with the transcription or translation of the given polynucleotide sequence (e.g., a promoter of a polynucleotide encoding FR polypeptide), where the antisense polynucleotide is capable of hybridizing to a FR polypeptide-encoding polynucleotide sequence. Of particular interest are antisense polynucleotides capable of inhibiting transcription and/or translation of a FR-encoding polynucleotide either in vitro or in vivo.

By "transformation" is meant a permanent or transient genetic change induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

By "construct" is meant a recombinant nucleic acid, generally recombinant DNA, that has been generated for the purpose of the expression of a specific nucleotide sequence (s), or is to be used in the construction of other recombinant nucleotide sequences.

As used herein the term "isolated" is meant to describe a compound of interest (e.g., a virus, a peptide, etc.) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, preferably 75% free, and most preferably 90% free from other components with which it is naturally associated.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease, or which may be susceptible to the disease, but has not yet been diagnosed as having it (e.g., where the subject is susceptible to infection by a pathogen, but has not yet been infected by the pathogen), including, but not limited to, reducing the risk of disease and/or death following infection by a filovirus; reducing the incidence of disease and/or death following infection by a filovirus; reducing the incidence or risk of infection by a filovirus; and reducing the extent of disease following infection by a filovirus; (b) inhibiting the disease, i.e., arresting its development, slowing its progression; and (c) relieving the disease, i.e., causing regression of the disease.

A "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids and tissue samples.

The term "immunologically active" refers to the capability of a natural, recombinant or synthetic FR polypeptide, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal.

The term "mimetic," as used herein, refers to a non-natural compound which exhibits one or more properties of a naturally occurring compound.

DESCRIPTION OF THE SPECIFIC EMBODIMENTS

Methods and compositions are provided for at least slowing the progression of a filovirus mediated disease condition in a host. In the subject methods, an effective amount of an agent that at least reduces the amount of folate receptor-mediated filovirus cell entry is administered to the host. The subject methods find use in both the prevention and treatment of filovirus associated disease conditions, including Marburg and Ebola-Zaire virus mediated disease conditions.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Methods of Treating a Filovirus-Mediated Disease Condition

The present invention provides methods of treating a filovirus-mediated disease condition in an individual. The methods generally comprise administering to an individual an effective amount of an agent that reduces a level of folate receptor-mediated viral entry into a cell in the individual. In some embodiments, the invention provides methods of inhibiting binding of a filovirus to an FR receptor on the surface of a susceptible cell. In other embodiments, the invention provides methods for reducing a level of FR receptor on the surface of a cell that normally expresses FR receptor on its cell surface. In other embodiments, the invention provides methods for modulating an FR receptor on a surface of a cell such that filovirus binding to the FR receptor is reduced.

As used herein, the term "filovirus" refers to any known filovirus, including but not limited to, Marburg virus and Ebola virus, and subtypes of any known filovirus. Four subtypes of Ebola virus have been identified: Ivory Coast, Sudan, Zaire, and Reston. The nucleotide sequence of the complete genome of Ebola virus is found under GenBank Accession number NC_002549. The nucleotide sequence of the complete genome of Marburg virus is found under GenBank Accession No. NC_001608.

It has now been found that filovirus entry into a susceptible cell is mediated by a folate receptor (FR), e.g., folate receptor alpha (FRα). A "susceptible cell" (also referred to herein as a "permissive cell") is therefore any eukaryotic cell which expresses a FR on its cell surface such that a filovirus can bind to the cell surface FR and enter the cell. In general, a susceptible cell is a primate cell, e.g., a human cell or a monkey cell. A "susceptible cell" includes, but is not limited to, a susceptible in an animal, e.g., a primate; a susceptible cell in an organ from the animal (e.g., an organ removed from the animal); a susceptible cell in a biological sample derived from an animal; a susceptible cell in in vitro culture, e.g., a cell isolated from an animal; a susceptible cell which is made susceptible by virtue of having been transformed with a nucleic acid construct comprising a nucleic acid sequence that encodes a FR, e.g. cell line which does not normally express FR on its cell surface but which does so after introduction into the cell line of a construct which results in expression of FR on the cell surface, as described in the Examples; and a susceptible cell which is a cell line that is naturally permissive to filovirus infection, including, but not limited to, HeLa cells and VeroE6 cells.

Whether a cell is susceptible to infection by a filovirus can be determined by any known method, including those described in the Examples.

The methods generally comprise administering to an individual an effective amount of an agent that reduces a level of folate receptor-mediated viral entry into a susceptible cell in the individual. In some embodiments, an "effective amount" of an agent that reduces FR-mediated entry into a cell is one that reduces filovirus entry into a susceptible cell by at least about 10%, at least about 20%, at least about 30%, at least about 40%, at least about 50%, at least about 60%, at least about 70%, at least about 80%, at least about 90, or at least about 100%, when compared to a susceptible cell in the absence of the agent. In other embodiments, an "effective amount" of an agent is contacted with a population of susceptible cells, where an "effective amount" is an amount that reduces the proportion of cells in the population that is infected by the filovirus by at least about 10%, at least about 20%, at least about 30%, at least about 40%, at least about 50%, at least about 60%, at least about 70%, at least about 80%, at least about 90, or at least about 100%, when compared with the population not contacted by the agent.

It has further been shown that filovirus entry into a susceptible cell can be inhibited by inhibiting binding of a filovirus to a FR on the surface of a susceptible cell. Accordingly, in some embodiments, a method of treating a filovirus-mediated disease condition in an individual comprises administering to an individual an effective amount of a substance that inhibits binding of a filovirus to a FR on the surface of a susceptible cell in the individual. As used herein, the term "agent" refers to any substance that inhibits binding of a filovirus to FR, including, but not limited to, antibody specific for FR; folic acid and its derivatives; and soluble FR. Generally, these methods involve blocking a binding event between a filovirus and an FR. The methods provide for inhibiting binding of a filovirus to an FR on the surface of a susceptible cell by at least about 10%, at least about 20%, at least about 30%, at least about 40%, at least about 50%, at least about 60%, at least about 70%, at least about 80%, at least about 90%, or at least about 100%, when compared to the amount of filovirus that binds to an FR on the surface of a control cell, e.g., a cell not contacted with the agent.

In other embodiments, the invention provides methods for reducing a level of FR receptor on the surface of a cell that normally expresses FR receptor on its cell surface, comprising contacting the cell with an effective amount of an agent that reduces a level of FR on the cell surface. In these embodiments, an "effective amount" of an agent is an amount that is effective in reducing the level of FR on the cell surface by at least about 10%, at least about 20%, at least about 30%, at least about 40%, at least about 50%, at least about 60%, at least about 70%, at least about 80%, at least about 90%, or at least about 100%, when compared to the level of FR expressed on the cell surface of a control cell not contacted with the agent. The level of FR on the cell surface can be determined (e.g., measured) using any known method, including, but not limited to, contacting a cell with a detectably labeled antibody specific for FR, and determining the amount of bound antibody using, e.g., fluorescence activated cell sorting (FACS), radioligand binding, immunofluorescence, Northern (RNA) blotting, Western (protein) blotting, and in situ hybridization.

Reduction in a level of FR receptor displayed on the surface of a cell that normally expresses FR receptor on its cell surface may be accomplished by a variety of means, including, but not limited to, reducing the level of transcription of a gene encoding the FR; reducing the level of FR-encoding mRNA available to be translated; reducing the level of translation of an FR-encoding mRNA; reducing formation of a GPI linkage on the FR, thereby resulting in secretion of the FR from the cell, rather than placement in the cell membrane; reducing the rate and/or level of any cell biological process that normally results in expression of FR on the cell surface. In some cases it may be preferably that the method is specific or relatively specific to FR, e.g., the method does not reduce the level of any other protein on the cell surface.

Reduction in expression of an FR-encoding gene may be accomplished by using antisense to the FR-encoding gene. Various derivatives of the antisense sequence may be prepared, where the phosphates may be modified, where oxygens may be substituted with sulfur and nitrogen, the sugars may be modified, and the like. The antisense sequences may be used by themselves or in conjunction with various toxic moieties, such as metal chelates, sensitizers, ribozymes, and the like. Antisense and/or ribozyme sequences may be used to inhibit FR gene expression. Antisense polynucleotides, and methods of using such, are described in numerous publications, including, e.g., "Antisense Technology: A Practical Approach" Lichtenstein and Nellen, eds. (1997) IRL Press.

Antisense molecules can be used to down-regulate expression of FR-encoding genes in cells. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise two or more different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra.) Preferred oligonucleotides are chemically modified from the native phosphodiester structure, in order to increase their intracellular stability and binding affinity. Such modifications have been previously discussed with respect to the use of probes.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

In other embodiments, the invention provides methods for modulating an FR receptor on a surface of a cell such that filovirus binding to the FR receptor is reduced. The agent may modulate the configuration of the surface membrane-associated FR such that it no longer binds filovirus. Alternatively, the agent may be one that modulates trafficking, clustering, or internalization of FR. The agent may be one that inhibits glycosylation of FR. Roberts et al. (1998) *Arch. Biochem. Biophys.* 351:227–235.

In any of the above-described methods of the invention for treating a filovirus-mediated disease condition, more than one agent may be administered to an individual in need of treatment. Thus, for example, a mixture of two or more monoclonal antibodies specific for distinct, non-overlapping epitopes on an FR may be administered to the individual. Mixtures of two or more different agents, e.g., a monoclonal antibody specific for an FR and a folate receptor ligand, may also be administered.

Routes of Administration

An agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent used and/or the desired effect. A composition comprising an agent can be administered in a single dose or in multiple doses.

An agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An agent can also be delivered to the subject by enteral administration. Enteral routes of administration include, but are not necessarily limited to, oral and rectal (e.g., using a suppository) delivery.

Methods of administration of an agent through the skin or mucosa include, but are not necessarily limited to, topical application of a suitable pharmaceutical preparation, transdermal transmission, injection and epidermal administration.

The invention also contemplates opthalmic administration of an agent, which generally involves invasive or topical application of a pharmaceutical preparation to the eye. Eye drops, topical cremes and injectable liquids are all examples of suitable formulations for delivering drugs to the eye.

Dosages

Although the dosage used will vary depending on the clinical goals to be achieved, a suitable dosage range is one which provides up to about 1 $\mu$g to about 1,000 $\mu$g or about 10,000 $\mu$g of agent can be administered in a single dose. Alternatively, a target dosage of agent can be considered to be about 1–10 $\mu$M in a sample of host blood drawn within the first 24–48 hours after administration of the agent.

In general, an agent is administered in an amount within the range from about 0.002 mg/kg to about 10 mg/kg, or from about 0.01 mg/kg to about 3 mg/kg body weight. Where an agent is to be administered intravenously, it will be formulated in conventional vehicles, such as distilled water, saline, Ringer's solution or other conventional carriers.

Methods for Immunizing a Host

The invention further provides methods for immunizing a host against a filovirus mediated disease condition. In general, the methods involve administering to a host an effective amount of an immunogen that causes said host to mount an immune response against membrane bound folate receptors, where antibodies are generated that inhibit filovirus binding to the FR, thereby reducing entry of the filovirus into a permissive cell. In some embodiments, the immunogen is a membrane bound folate receptor or fragment thereof. Methods of generating an immune response in a host are known in the art and need not be elaborated upon here. Whether an individual has mounted an immune response to a membrane bound folate receptor can be readily determined. For example, a biological sample, such as a blood or serum sample, is removed from the individual, and the presence of antibodies that specifically bind to membrane bound FR and block or inhibit filovirus binding to the FR is detected using assays such as those described in the Examples.

Antibodies generated in a human in the manner described above may be isolated and used prophylactically in a passive immunization protocol to protect another human against a filovirus-mediated disease condition. For example, a health care worker or other medical personnel or support staff who anticipate being in a situation which puts him/her at risk for exposure to filovirus may be treated prophylactically with anti-FR antibodies generated in another human. In some instances, e.g., where medical personnel is exposed to filovirus for a short period, e.g., 1–7 days, or 1–4 weeks, short-term protection of such individuals, such as may be afforded by passive immunization, may be adequate to protect the individual from filovirus infection, or may reduce symptoms during infection (e.g., attenuation of disease).

Method for Identifying a Viral Cell Surface Receptor

The invention provides a method of a identifying a cell surface receptor used by a virus for entry into a cell. The methods generally comprise: (a) identifying a cell line that is non-permissive for entry of the virus; (b) transfecting a population of said non-permissive cell line with a genomic or a cDNA library obtained from a cell line permissive for entry of the virus; (c) identifying at least one cell from said transfected cell population which is permissive for entry of the virus; and (d) identifying at least one gene of the permissive cell line in the genome of the transfected permissive cell. These methods are useful for identifying a cell surface receptor for a filovirus. In particular embodiments, a population of non-permissive cells is transfected with a cDNA library made from a permissive cell such that a member of the cDNA library are expressed in a cell of the transfected non-permissive cell population. To determine which cell(s) of the transfected non-permissive population are now permissive for filovirus infection, a pseudotype virus may be employed, in which an envelope-negative mutant virus carrying a selectable marker is engineered to contain a filovirus envelope glycoprotein. In a particular embodiment, a pseudovirus as described in the Examples is used.

Agents Effective for Treating a Filovirus-Mediated Disease Condition

The present invention provides agents for treating a filovirus-mediated disease condition. In some embodiments, an agent that is suitable for treating a filovirus-mediated disease condition is one that inhibits binding of a filovirus to an FR$\alpha$ on the surface of a susceptible cell. As used herein, "an FR antagonist" is any agent that inhibits a binding event between a filovirus and a membrane-bound FR, including, but not limited to, a soluble FR, an antibody specific for an FR, a filovirus-derived FR ligand, an FR ligand, and a fragment, derivative, or mimetic of any of the foregoing. In other embodiments, an agent is one that modulates trafficking, clustering, or internalization of membrane bound folate receptors. In other embodiments, an agent is one that modulates expression or configuration of a membrane-bound folate receptor such that binding to a filovirus is reduced.

Folic Acid Receptor

FR is a protein encoded by a gene that is a member of the folate receptor family. Members of this gene family have a high affinity for folic acid and for several reduced folic acid derivatives, and mediate delivery of 5-methyltetrahydrofolate to the interior of eukaryotic cells. The gene is composed of 7 exons: exons 1–4 encode the 5' untranslated region and exons 4 through 7 encode the open reading frame. Due to the presence of 2 promoters, multiple transcription start sites, and alternative splicing of exons, at least 8 transcript variants are derived from this gene. These variants differ in the length of 5' and 3' UTR, but they encode an identical amino acid sequence. Elwood et al. (1997) *Biochem.* 36: 1467–1478.

Human FRα (also referred to as folate binding protein) is synthesized in cells as an integral membrane-associated protein and as a soluble protein. Sadavisan and Rothenberg (1989) *J. Biol. Chem.* 264:5806–5811. The amino acid sequence of human FRα is provided under GenBank Accession No. NM_016731. The membrane-associated form is a glycosyl phosphatidyl inositol linked protein, while the secreted form lacks the GPI moiety. Nucleotide and amino acid sequences of FR from other species are also publicly available under GenBank.

As used herein, the terms "folate receptor" and "folate binding protein" are used interchangeably herein and refer to FR from any of a variety of species, including, but not limited to, human, murine (mouse or rat), bovine, or other mammalian species. In some embodiments, an FR is a human FRα having the amino acid sequence set forth in GenBank Accession No. NM_016731. In some embodiments, an FR is a polypeptide comprising an amino acid sequence that shares at least about 50%, at least about 60%, at least about 75%, at least about 80%, at least about 90%, or at least about 95% or more sequence identity with the sequence set forth in GenBank NM_016731. It is generally preferred that the FR administered to the individual does not elicit an immune reaction in the individual to the FR. "FR" also encompasses fragments of an FR that inhibit binding of a filovirus to an FR on the surface of a susceptible cell. Full length FR is a protein of about 226 amino acids. In some embodiments, FR is a fragment of from about 15 to about 20, from about 20 to about 25, from about 25 to about 50, from about 50 to about 75, from about 75 to about 100, from about 100 to about 125, from about 125 to about 150, from about 150 to about 175, or from about 175 to about 200 amino acid, up to the full length protein. "FR" also encompasses fusion proteins, wherein an FR is fused in-frame to a fusion partner which is a heterologous protein, i.e., a non-FR protein. Fusion partners include, but are not limited to, immunological tags, cytokines, carrier proteins (e.g., albumin), antibody (including antibody fragments), cytotoxic agents, protein domains that cause multimerization, and the like.

"FR" may be an FR isolated from a source in which it naturally occurs, may be a synthetic FR, or may be an FR made recombinantly. "FR" also encompasses mimetics of a naturally occurring FR, and peptoids. Methods of synthesizing peptoids, and peptoid libraries, and methods of screening same are found in, e.g., U.S. Pat. Nos. 5,965,695; and 6,075,121.

FR may be made recombinantly using standard techniques of molecular biology; may be made synthetically using standard techniques of protein synthesis; may be isolated from a source in which it naturally occurs (e.g., milk or other body fluids); or a combination of any of the foregoing. FR polypeptides can be isolated from a biological source, using affinity chromatography, e.g., using antibodies specific for FR which are immobilized on a solid support.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae,* insect cells in combination with baculovirus vectors, or cells of a higher organism such as vertebrates, particularly mammals, e.g. COS 7 cells, CHO cells, HEK293 cells, HeLa cells, and the like, may be used as the expression host cells. In some situations, it is desirable to express the gene in eukaryotic cells, where the protein will benefit from native folding and post-translational modifications. The polypeptide can then be isolated from cell culture supernatant or from cell lysates using affinity chromatography methods or anion exchange/size exclusion chromatography methods, as described above.

One may employ solid phase peptide synthesis techniques, where such techniques are known to those of skill in the art. See Jones, The Chemical Synthesis of Peptides (Clarendon Press, Oxford)(1994). Generally, in such methods a peptide is produced through the sequential additional of activated monomeric units to a solid phase bound growing peptide chain.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique.

For use in the methods of the invention, an FR may be administered in a formulation in association with (e.g., chemically associated, or in admixture with) another macromolecule, including, but not limited to, a protein, including, but not limited to, albumin; a nanoparticle; a lipid, including, but not limited to liposomes; a polysaccharide; a polyalcohol, including, but not limited to, a polyethylene glycol; a glycoprotein; and combinations of the foregoing.

Folate Receptor Ligands

Agents that inhibit binding of a filovirus to a membrane bound FR also include folate receptor ligands, and derivatives and mimetics thereof. A folate receptor ligand may be folic acid (5-methyl tetrahydrofolic acid); or a derivative thereof, including, but not limited to, dihydrofolate, tetrahydrofolate, 5-methyltetrahydrofolate, 5,10-methylenetetrahydrofolate, 5,10-methenyltetrahydrofolate, 5,10-formiminotetrahydrofolate, 5-formyltetrahydrofolate (leucovorin), and 10-formyltetrahydrofolate.

Filovirus-derived Folate Receptor Ligands

Agents that inhibit binding of a filovirus to a membrane-bound FR further include filovirus molecules that bind to FR, which reduce binding of a filovirus to the FR, and which therefore reduce FR-mediated filovirus entry into a permissive cell. Filovirus-derived folate receptor ligands include, but are not limited to, a filovirus envelope glycoprotein. Marburg envelope glycoprotein is described in Xu et al. (1998) *Nat. Med.* 4: 37–42; and Ebola virus Zaire envelope glycoprotein is described in GenBank accession number U31033. "Filovirus envelope glycoprotein," as used herein in the context of an agent that inhibits binding of a filovirus to a membrane-bound FR, encompasses full-length filovirus envelope glycoprotein (GP); fragments of a filovirus envelope GP which mediate binding to an FR; fusion proteins comprising the filovirus envelope GP (or fragment thereof. Those skilled in the art, using any known method, including those described herein, can readily determine any fragment of a filovirus envelope glycoprotein that can inhibit binding of a filovirus to a membrane-bound FR.

Antibodies

An agent that inhibits binding of a filovirus to an FR on the surface of a susceptible cell may be an antibody. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme that generates a detectable product, a green fluorescent protein, and the like. The antibodies may be further conjugated to other moieties, such as members of specific binding pairs, e.g., biotin (member of biotin-avidin specific binding pair), and the like.

Methods of generating an antibody to an FR are well known in the art and need not be elaborated upon herein. Such methods are found in a variety of standard textbooks, such as *Antibodies: A Laboratory Manual,* E. Harlow and D. Lane, eds. 1988, Cold Spring Harbor Laboratory Press. Antibodies generated to an FR may be screened for the ability to inhibit binding of a filovirus to an FR, using, e.g., the methods described in the Examples.

Agent that Modulate Trafficking, Clustering, or Internalization of Membrane Bound Folate Receptors Agents that modulate trafficking, clustering, or internalization of membrane-bound FR include, but are not limited to, an agent that inhibits or interferes with glycolipid anchors, e.g., phospholipase-C; an agent that inhibits or interferes with glycosylation of an FR; agents that disrupt the pathway to construct GPI anchors in the endoplasmic reticulum; agents that disrupt acidification of vesicles; agents that inhibit recycling of GPI-linked proteins such as FR; agents that prevent multimerization of FR at the cell surface (e.g., FR fragments that bind to multimerization domains; and agents that prevent endocytosis of FR or GPI-linked proteins.

Agents that Modulate Expression or Configuration of a Membrane-bound Folate Receptor such that Binding to a Filovirus is Reduced Agents that modulate expression or configuration of a membrane-bound folate receptor such that binding to a filovirus is reduced include, but are not limited to, antisense molecules (as discussed above); ribozymes (as discussed above); compounds that selectively reduce transcription of a FR gene; and dominant-negative forms of FR which reduce and/or prevent proper binding, folding, or multimerization of FR on the cell surface.

Compositions

The present invention further provides compositions comprising an agent of the invention. These compositions may include a buffer, which is selected according to the desired use of the agent, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

Pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Screening Assays

The present invention provides methods of screening for candidate agents that are useful in treating a filovirus-mediated disease condition. In some embodiments, methods are provided for screening for candidate agents that inhibit binding of a filovirus to a FR on the surface of a susceptible cell. In other embodiments, methods are provided for screening for candidate agents that reduce a level of FR on the surface of a susceptible cell.

The term "candidate agent" is used interchangeably herein with the terms "candidate substance" and "candidate compound". A "candidate agent," as used herein, describes any molecule, e.g. protein; peptide; natural or synthetic inorganic or organic compound, or pharmaceutical, with the capability of reducing filovirus entry into a susceptible cell, as described above. Generally a plurality of assay mixtures is run in parallel with different agent concentrations to obtain a differential response to the various concentrations. Typically, one of these concentrations serves as a negative control, i.e. at zero concentration or below the level of detection.

Candidate agents encompass numerous chemical classes, and may be natural or synthetic inorganic or organic molecules, which may be small organic compounds having a molecular weight of more than 50 and less than about 2,500 daltons. Candidate agents may comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, glycosylation, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Methods of Identifying Candidate Agents that Inhibit Filovirus Binding to FR

In some embodiments, methods are provided for identifying a candidate agent that inhibits filovirus binding to FR. In some of these embodiments, the methods are cell-free methods. In other embodiments, the methods are cell-based methods. In general, the methods described below are in vitro screening methods. Candidate agents identified by the methods described below include those that act to block binding of a filovirus to an FR; and those that act to modulate a configuration of an FR such that filovirus binding is reduced. Candidate agents of interest are those that reduce filovirus entry into a cell. Accordingly, in some embodiments, the methods provide for identifying a candidate agent that reduces filovirus entry into a cell.

As used herein, "determining" includes "measuring" and "detecting," e.g., the determination may be quantitative or semi-quantitative (e.g., "measuring") or qualitative (e.g., "detecting").

Agents which decrease FR-filovirus binding to the desired extent may be selected for further study, and assessed for cellular availability, cytotoxicity, biocompatibility, etc.

Of interest are candidate agents that inhibit FR-filovirus binding by at least about 10%, at least about 15%, at least about 20%, at least about 25%, more preferably at least about 10%, at least about 15%, at least about 20%, at least about 25%, at least about 50%, at least about 100%, or 2-fold, at least about 5-fold, or at least about 10-fold or more when compared to a suitable control. A candidate agent which inhibits FR-filovirus binding can also be one that abrogates measurable FR-filovirus binding completely.

Also of interest are candidate agents that reduce filovirus entry into a cell susceptible to filovirus infection by at least about 10%, at least about 15%, at least about 20%, at least about 25%, at least about 50%, at least about 100%, or 2-fold, at least about 5-fold, or at least about 10-fold or more when compared to a suitable control. A candidate agent which inhibits FR-filovirus entry can also be one that abrogates measurable FR-filovirus entry completely.

Also of interest are candidate agents that reduce the number of cells in a population of susceptible cells that are infected by filovirus by at least about 10%, at least about 15%, at least about 20%, at least about 25%, at least about 50%, or at least about 100%, when compared to a suitable control.

Cell-free Methods

A cell-free method to identify candidate agents that inhibit binding of a filovirus to an FR generally comprise:

a) contacting a candidate agent with a sample containing an FR and a filovirus; and b) determining whether binding between the FR and the filovirus is reduced.

In some embodiments, the screening methods will employ a filovirus envelope glycoprotein. Thus, the term "filovirus," in the context of screening assays of the invention, encompasses a filovirus envelope glycoprotein. Thus, in these embodiments, the methods comprise contacting a candidate agent with a sample containing an FR and a filovirus envelope glycoprotein; and determining whether FR-filovirus envelope glycoprotein binding is reduced, compared to binding in the absence of the candidate agent.

Marburg envelope glycoprotein is described in Xu et al. (1998) *Nat. Med.* 4: 37–42; and Ebola virus Zaire envelope glycoprotein is described in GenBank accession number U31033. "Filovirus envelope glycoprotein," as used herein, encompasses full-length filovirus envelope glycoprotein (GP); fragments of a filovirus envelope GP which mediate binding to an FR; fusion proteins comprising the filovirus envelope GP (or fragment thereof), including, but not limited to, epitope-tagged filovirus envelope GP. In addition, the filovirus envelope GP may be detectably labeled.

Determining whether FR-filovirus binding is reduced can be accomplished in a variety of ways, including, but not limited to, any known immunological assay method, including, but not limited to, an immunological assay in which FR-filovirus binding is detected using antibody to the FR, to the filovirus (where the antibody is not one that inhibits FR-filovirus binding), to an epitope tag moiety of an FR fusion protein, or to an epitope tag moiety of a filovirus envelope GP; an enzyme-linked immunological assay; an immunological assay in which the FR and/or the filovirus is detectably labeled.

Cell-based Assays

In some embodiments, the screening assays are cell-based assays. In some of these embodiments, the methods generally comprise contacting a cell susceptible to infection by a filovirus with a candidate agent; and determining an effect, if any, on filovirus binding to the cell. In other of these embodiments, the methods generally comprise contacting a cell susceptible to infection by a filovirus with a candidate agent; and determining an effect, if any, on filovirus entry into the cell.

Cells suitable for use in these methods are any permissive eukaryotic cell, including cells that are naturally permissive, including, but not limited to, those cells shown in FIG. 2 that were shown to be permissive for filovirus infection (e.g., HOS, HeLa, VeroE6, CHO; and cells that are modified to be permissive for filovirus entry, including, but not limited to, cells as described in the Examples.

In some embodiments, a pseudotype virus, e.g., an HIV-1 virus engineered to contain a nucleotide sequence encoding a filovirus envelope glycoprotein, such as described in the Examples, may be employed. Thus, in the context of a cell-based screening assay of the invention, "filovirus" encompasses pseudotype virus comprising a nucleotide sequence encoding a filovirus envelope glycoprotein.

Whether filovirus binds to and enters the cell can be determined using any known assay method, including, but not limited to, assays described in the Examples. As described in the Examples, a pseudotype virus can be engineered to comprise a filovirus envelope GP and a nucleotide sequence encoding a selectable marker, or a detectable gene product (e.g., luciferase, GFP, and the like). Filovirus entry into the cell can then be determined by, e.g., measuring the amount of detectable gene product in the cell. The assay can also be conducted so as to determine the number of cells in a cell population that are infected.

Methods of Screening for Candidate Agents that Reduce a Level of FR on the Surface of a Susceptible Cell In general, methods for reducing a level of FR on the surface of a susceptible cell comprise contacting a susceptible cell with a candidate agent; and determining the effect, if any, on the level of FR on the surface of the cell.

Cells which may be employed are as described above, and are generally cells that are susceptible to filovirus infection by virtue of expressing an FR on the cell surface. Methods for determining whether a candidate agent reduces a level of FR on the cell surface include methods of measuring or detecting filovirus entry into the cell, as described above.

Determination of whether a candidate agent reduces FR gene expression can be carried out using any known assay. For example, a polymerase chain reaction (PCR) can be carried out on mRNA isolated from a cell, using a primer pair specific for an FR-encoding transcript. A cDNA copy of the population of isolated mRNA, and PCR performed on the cDNA. Another method which may be employed involves an assay in which a cell is transfected with a construct comprising an FR promoter driving transcription of a reporter gene, and the effect of the candidate agent on the level of transcription of the reporter gene is determined.

The following examples are offered by way of illustration and not by way of limitation. The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celcius, and pressure is at or near atmospheric.

EXPERIMENTAL

EXAMPLE 1

Identification of a Cofactor for Entry of Marburg and Ebola Viruses into Susceptible Cells Materials and Methods Cell lines. Human osteosarcoma (HOS), HeLa, 293T, Vero E6, and CHO-K1 cells were cultured as recommended by the American Type Culture Collection (ATCC). Jurkat T-cells stably expressing the ecotropic murine leukemia virus (MLV) receptor (Jurkat-EctR, kindly provided by Dr. G. Nolan, Stanford University) were cultured as recommended for Jurkat T-cells by the ATCC. The NIH-3T3 based MLV packaging cell line PT67 (Clontech, Palo Alto, Calif.) was cultured as previously described (Miller and Chen (1996) J. Virol. 70, 5564–5571. Human osteosarcoma (GHOST) indicator cell lines carrying a human green fluorescent protein (GFP) reporter gene driven by an HIV-2 Tat-dependent LTR (provided by Dr. D. Littman, Skirball Institute) were cultured as previously described (Trkola et al., (1998) J. Virol. 72, 1876–1885).

Plasmids and cDNA library amplification The molecular clone pNL-Luc-E$^-$R$^-$(Connor et al., (1995) Virology 206, 935–944), the HIV-1 NL4–3 provirus carrying a luciferase reporter gene driven by the 5' LTR (along with mutations in env, nef, and vpr), was a gift of Dr. N. Landau (Salk Institute) via the AIDS Research and Reference Reagent Program. HIV-blasti, an HIV-1 proviral construct carrying the blasticidin S deaminase gene driven by the 5' LTR along with null mutations in env and nef was provided by Dr. R. Sutton (Baylor University). Mammalian expression plasmid pVSV-G encoding the vesicular stomatitis virus-G (VSV-G) protein was provided by Dr. J. Burns (University of California, San Diego), and pMULV-A encoding the amphotropic (Ampho) murine leukemia virus (MLV) env (Landau et al., (1991) J. Virol. 65, 162–169) was provided by Dr. K. Page (University of California, San Francisco). The cDNA clones encoding MBG GP and EBO-Z GP were provided by Dr. A. Sanchez (Centers for Disease Control and Prevention) and cloned into the pCMV4neo expression vector (Goldsmith et al., (1994) J. Biol. Chem. 269, 14698–14704) as previously described (Chan et al., (2000) J. Virol. 74, 4933–4937). The full length and 3' truncated cDNA (E4-1) encoding FR-α was recovered by PCR from the HeLa retroviral library as described below, ligated by TA cloning into pCR2.1, and subcloned into the mammalian expression vector. The bicistronic mammalian expression vector pIRES2-EGFP (Clontech, Palo Alto, Calif.) was used to assess transfection efficiency in Jurkat-EctR cells.

A bacterial glycerol stock transformed with the MLV retroviral cDNA library (pLib MLV backbone) derived from HeLa cells ($2 \times 10^6$ independent clones) was plated on LB agar (100 µg/ml ampicillin) plates as described by the manufacturer (Clontech, Palo Alto, Calif.). Approximately $8 \times 10^6$ bacterial colonies were amplified in LB liquid broth, and library DNA was extracted for subsequent virus packaging and transduction into Jurkat-EctR cells. The plasmid pLib-GFP encoding the green fluorescent protein in the MLV backbone was used as a marker for quantitating efficiency of transduction.

Antibodies. For detection of wildtype MBG virus infection, convalescent guinea pig antisera to MBG virus (Musoke) was generated. FITC-conjugated anti-guinea pig secondary antisera was purchased. For inhibition of pseudotype virus entry, polyclonal rabbit antisera raised against FBP in bovine milk (Biogenesis, Poole, England, UK) and normal rabbit sera (kindly provided by Dr. O. Keppler, Gladstone Institute of Virology and Immunology, CA) were compared. Similarly, monoclonal mouse IgG1 ascites raised against human FR-α (kindly provided by Dr. W. Franklin, University of Colorado Health Sciences Center) and monoclonal mouse IgG1 ascites raised against HIV-1 Gag p24 antigen were compared. For assessing binding of FBP to CHO-K1 cells expressing virus GP by immunofluorescence, polyclonal goat anti-bovine FBP antibody and fluorescein-conjugated rabbit anti-goat IgG Fc were used for staining (Rockland, Gilbertsville, Pa.).

Preparation of pseudotype virus stocks. To prepare HIV-1 pseudotype virus carrying the luciferase gene (Luc$^+$) with the Ampho, VSV-G, MBG, or EBO-Z GP, pNL-Luc-E$^-$R$^-$ (2 µg/well) was co-transfected with each envelope glycoprotein expression vector (2 µg/well) using the CaPO$_4$ method in 293T cells as previously described (Chan et al., (1999) J. Virol. 73, 2350–2358). To prepare selectable HIV-1 pseudotype virus carrying the blasticidin S deaminase gene (blasti), 293T cells (400,000 cells/well in 6-well plates) were transiently co-transfected using the CaPO$_4$ method with pHIV-blasti (2 µg/well) and an envelope GP expression vector encoding MBG GP (2 µg/well), EBO-Z GP (2 µg/well), or VSV-G GP (2 µg/well) as above. Viral stocks were sterile filtered (0.2 µm) and harvested after 36 h in a BSL3 facility.

Protocol for genetic reconstitution of permissivity to filovirus entry. To reconstitute permissivity for MBG virus entry, library DNA (3 µg/well) or pLib-GFP (3 µg/well) reporter plasmid was packaged into pseudovirions by transiently co-transfecting PT67 packaging cells (300,000 cells/well in 6-well plates) along with pVSV-G (1 µg/ml)

using the CaPO$_4$ method and harvesting culture supernatants on day 2 post-transfection. Subsequently, approximately 1.2×10$^8$ Jurkat-EctR cells were transduced with library-containing viral supernatants via spin infection (1.3×10$^6$ RPM, 32° C., 2 h) in 6 separate batches. In parallel, Jurkat-EctR cells were transduced with pseudovirions carrying pLib GFP. By quantitating GFP-positive Jurkat-EctR cells two days after transduction, library infection was optimized to achieve reproducible 30–40% transduction efficiency. Two days later, selectable MBG-blasti or VSV-blasti pseudotype virus was harvested and used to challenge parental cells or cells transduced with the library. In parallel, GHOST cells (250,000 cells/well) were inoculated with 1 ml of selectable pseudotype HIV virus, since they are permissive to entry by MBG, EBO-Z, and VSV viruses (Chan et al., (2000) J. Virol. 74, 4933–4937). GHOST cells express the GFP reporter only in the presence of HIV-1 Tat protein (Trkola et al., (1998) J. Virol. 72, 1876–1885), and thus after successful infection by HIV-1 pseudotype virions. Therefore, two days following challenge, by quantitating the percent of GFP-positive GHOST cells as previously described (Chan et al., (2000) J. Virol. 74, 4933–4937), relative levels of active MBG-blasti and VSV-blasti viruses were estimated as the percent of permissive cells that are infected using a given virus stock. When virus inocula achieved entry in more than 50% of the GHOST cell culture, the transduced Jurkat-EctR cells challenged with the same virus stock were transferred into medium containing blasticidin S (ICN, 40 μg/ml). After selection for 2 weeks, cells were monitored for viability by Trypan blue exclusion and counted on a hemacytometer. Selected cells were expanded and subjected to limiting dilution to obtain monoclonal cell populations.

To select for cells permissive to EBO-Z virus entry, a separate culture of 6 batches of Jurkat-EctR cells (total of 1.2×10$^8$ cells) were transduced with HeLa cDNA library following the above protocol. After 2 d, transduced cells were challenged with EBO-Z-blasti virus and selected in blasticidin S. Viable cells were detected in selected cultures by Trypan blue exclusion, expanded, and grown by limiting dilution as monoclonal cell populations.

Challenge of cells with pseudotype viruses and replication-competent filoviruses. To determine permissivity to entry by pseudotype viruses, Jurkat-EctR cells were plated in 24-well dishes (200,000 cells/well), incubated with constant inocula of HIV-1 Luc$^+$ pseudotype viruses for 48 h, and luciferase expression was quantitated as previously described ((Chan et al., (2000) J. Virol. 74, 4933–4937)).

To determine permissivity to entry by wildtype MBG virus, Vero-E6, parental Jurkat-EctR and reconstituted Jurkat-EctR (F10 clone) cells were inoculated with MBG (Musoke isolate) at increasing multiplicity of infection (MOI) of 0.1, 1, and 10. On days 1,3 and 6 post-infection cells were washed, dried on spot-slides, fixed with acetone, irradiated, and then immunostained with convalescent guinea pig antisera to MBG followed by FITC-conjugated anti-guinea pig antisera. Positive cells were counted by fluorescence microscopy.

To determine reconstitution of permissivity to MBG entry by expression of FR-α, parental Jurkat-EctR cells (1.5×10$^7$ cells) were electroporated (270 kV, 950 μF) with a mammalian expression vector (pCMV4neo) carrying no insert, a truncated (E4-1) cDNA, or full-length cDNA encoding FR-α. Transfection efficiency was quantitated in parallel using an expression plasmid encoding GFP (pIRES2-EGFP) and assessing percentage of GFP-positive cells by flow cytometry (10–20% positive). After recovery for 48 hours, transfected cells were plated in 24-well plates (300,000 live cells/well), challenged with pseudotype luciferase viruses, and luciferase expression was quantitated after 72 hours.

PCR recovery of retroviral library cDNA insert from transduced Jurkat-EctR cells. To recover cDNA library inserts from Jurkat-EctR cell clones permissive to MBG entry, genomic DNA was extracted by the "Easy DNA" method as instructed by the manufacturer (Invitrogen). Extracted DNA (50 ng) was used as template for PCR-based amplification using the Expand PCR kit (Roche Molecular Biochemicals, Indianapolis, Ind.) and oligonucleotide primers (Clontech, Palo Alto, Calif.) derived from the retroviral sequences flanking the cDNA inserts in the cDNA library. Specific DNA bands amplified in experimental samples, but not control samples, were extracted from agarose gels and used in conventional TA cloning steps using the pCR2.1 vector (Invitrogen). Insert sequences were verified by ABI Prism Dye terminator cycle sequencing (Perkin-Elmer, Foster City, Calif.) and were compared to known genomic and cDNA sequences using Entrez BLAST software.

To recover cDNA library inserts from Jurkat-EctR cell clones permissive to EBO-Z entry, total RNA was extracted from cells by the RNA STAT 60 method (Tel-Test, Inc., Friendswood, Tex.). Using total RNA as a template, RT-PCR was performed using ALV reverse transcriptase kit as recommended by the manufacturer (Roche Molecular Biochemicals) followed by PCR of resulting cDNA strands using the Expand PCR kit and primers derived from the same retroviral sequences flanking the library inserts as above. Subsequent cloning and sequencing of inserts were performed as described previously.

Inhibition of pseudotype virus entry by blocking FR-α on target cells. To cleave glycolipid membrane-anchored proteins such as FR-α from the cell surface, HeLa cells (30,000 cells/well in 24-well plates) or reconstituted Jurkat-EctR F10 cells (100,000 cells/well in 24-well plates) were pre-incubated with phospholipase C (ICN Pharmaceuticals, Inc., Costa Mesa, Calif.) for 2 h at 37° C. Cells were washed with phosphate buffered saline (PBS) and challenged with pseudotype luciferase viruses for 4 h at 37° C. Culture medium was then removed and replaced, followed by assessment of luciferase expression after 72 h.

To block epitopes necessary for binding ligand to FR-α using antibodies raised against FR-α, Jurkat-EctR F10 cells (100,000 cells/well in 24-well plates) or Vero E6 cells (30,000 cells/well in 24-well plates) were pre-incubated with media containing polyclonal rabbit anti-folate binding protein (FBP) or normal rabbit sera for 15 minutes at 4° C. Cells were then challenged in the presence of antisera with equivalent inocula of pseudotype luciferase viruses at 37° C. Luciferase expression was then quantitated after 72 h. Similarly, Jurkat-EctR F10 cells were pre-incubated with media containing monoclonal mouse anti-FR (IgG1) or monoclonal mouse anti-HIV Gag p24 (IgG1) for 15 minutes at 4° C. Cells were challenged with pseudotype luciferase viruses in the presence of antisera and luciferase expression was assessed as above.

To determine if epitopes on FR-α which bind its natural ligand folic acid are necessary for MBG or EBO-Z GP-mediated entry, virus challenge of target cells was performed in the absence of fetal bovine serum which carries high concentrations of folic acid. Therefore, 12 h after co-transfection of 293T cells with pNL-Luc E$^-$R$^-$ and envelope GP expression vector to produce pseudotype luciferase viruses, media was replaced with RPMI 1640 containing no fetal bovine serum (FBS) and no exogenously added folic acid (Life Technologies, Inc., Grand Island, N.Y.), and virus supernatant was harvested after 36 h. HOS target cells (30,000 cells/well in 24-well plates) were pre-incubated with RPMI 1640 in the absence of FBS and either in the absence or presence of exogenously added folic acid (1 mg/L) for 15 minutes at 4° C. Cells were then challenged with folic acid-free pseudotype luciferase viruses for 4 h at 37° C. Virus was removed, replaced with RPMI 1640 containing 10% fetal bovine serum and exogenous folic acid (1 mg/L), and luciferase expression was quantitated after 72 h.

Inhibition of pseudotype virus entry by binding virion GP with soluble FR-α (FBP). To competitively inhibit interaction of virion-anchored MBG or EBO-Z GP with membrane-anchored FR-α, soluble bovine FBP (FBP, Sigma, 1 mg/ml reconstituted stock in PBS) was pre-incubated with pseudotype virus supernatant harvested in RPMI 1640 in the absence of FBS or exogenous folic acid for 15 minutes at 4° C. HOS cells (30,000 cells/well in a 24-well plate) were challenged with virus in the presence of FBP (10 μg/ml final concentration) for 4 h at 37° C. Cells were then washed with PBS, media was replaced with Dulbecco's Minimum Essential Medium containing 10% FBS, and luciferase expression was assessed after 72 hours.

Binding of membrane-anchored MBG GP with FBP. To provide further evidence that MBG GP binds FR-α, CHO-K1 cells, which do not express detectable levels of FR-α, were transiently transfected with MBG GP or negative control Ampho GP (1 μg/well in a 6-well plate) using LipofectAMINE as described by the manufacturer (Life Technologies, Inc.). After 12 hours, transfected cells were trypsinized and replated (70,000 cells/chamber) on 4-well Permanox chamber slides (Nalge Nunc International, Naperville, Ill.) coated with poly-L-lysine (Sigma) as previously described (Allan, 2000) to ensure minimal cell detachment during staining. After 24 h, soluble bovine FBP (33 μg/ml) was incubated in the presence of a polyclonal goat anti-bovine FBP (250 μg/ml), known to be non-neutralizing for MBG entry, for 15 minutes at 4° C. in RPMI 1640 containing no FBS or exogenous folic acid. Transfected CHO-K1 cells were then incubated in the presence of the FBP/anti-FBP mixture or in the presence of anti-FBP alone for 30 minutes at 4° C. Cells were washed 3 times with ice cold PBS and fixed in 2% paraformaldehyde for 15 minutes at 4° C. After 3 washes with ice cold PBS, cells were incubated with fluorescein-conjugated rabbit anti-goat IgG Fc secondary antibody (4 μg/ml)) for 45 minutes at 25° C. in the dark. Cells were washed 3 times, mounted in Vectashield medium (Vector Laboratories, Inc., Burlingame, Calif.), and analyzed for staining by fluorescence microscopy.

Results

Figure 1B:
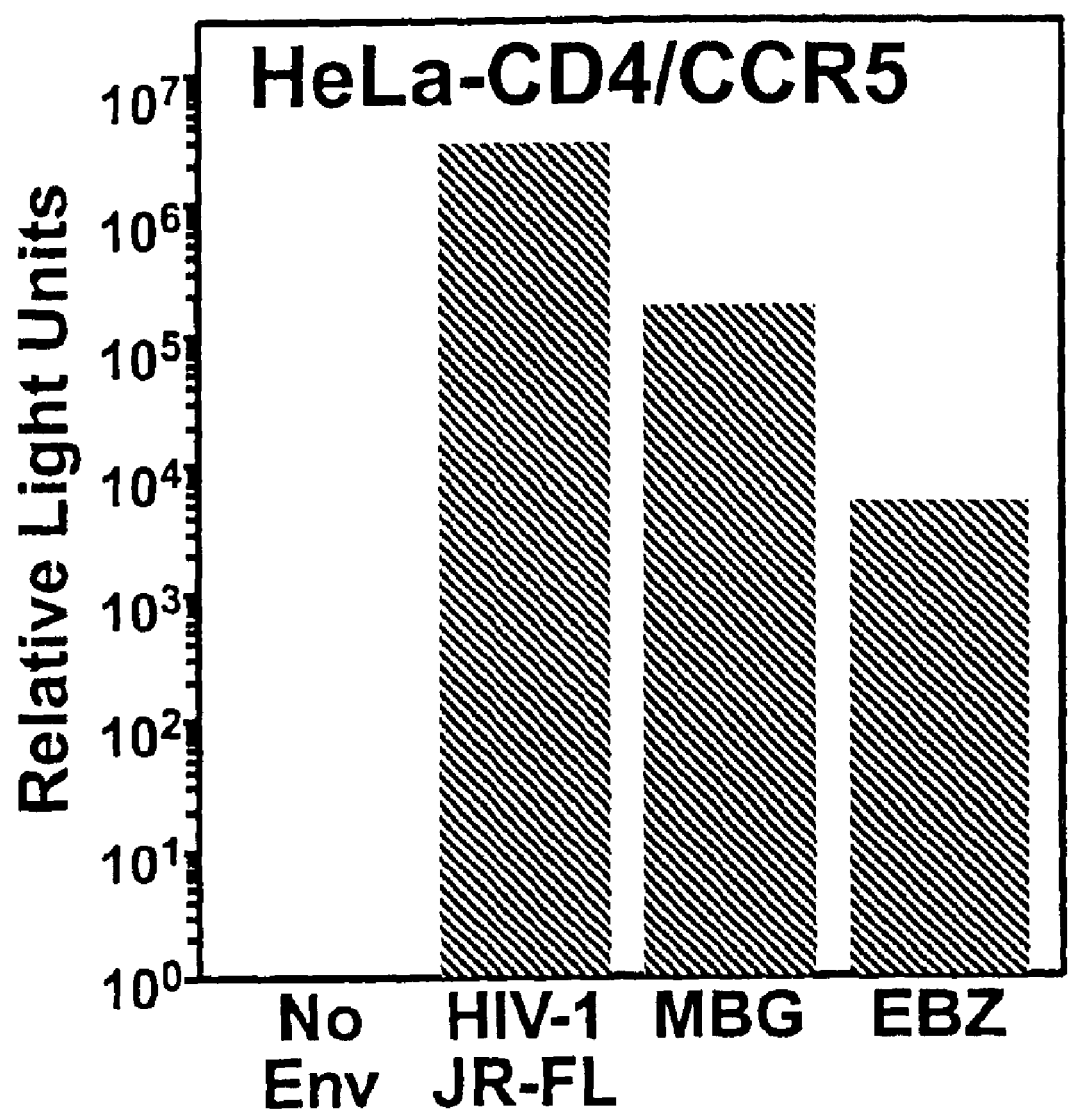
Figure 2A:
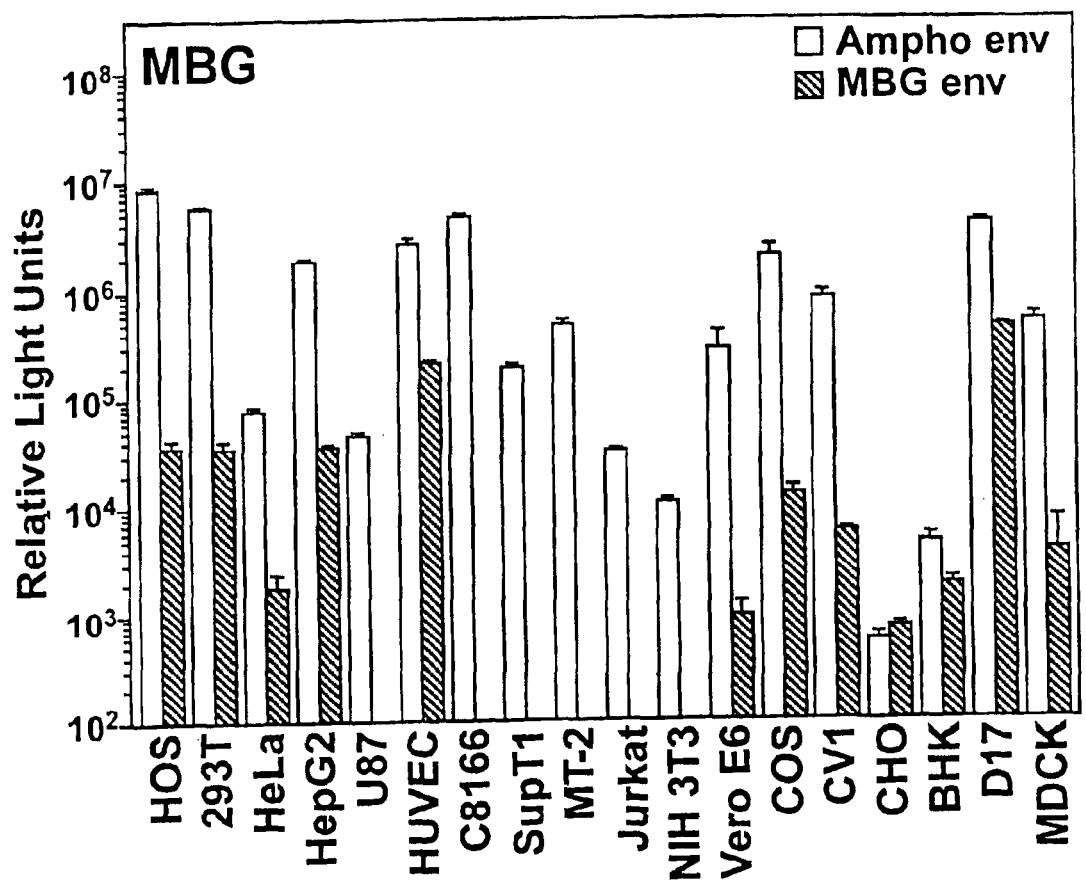
Figure 2B:
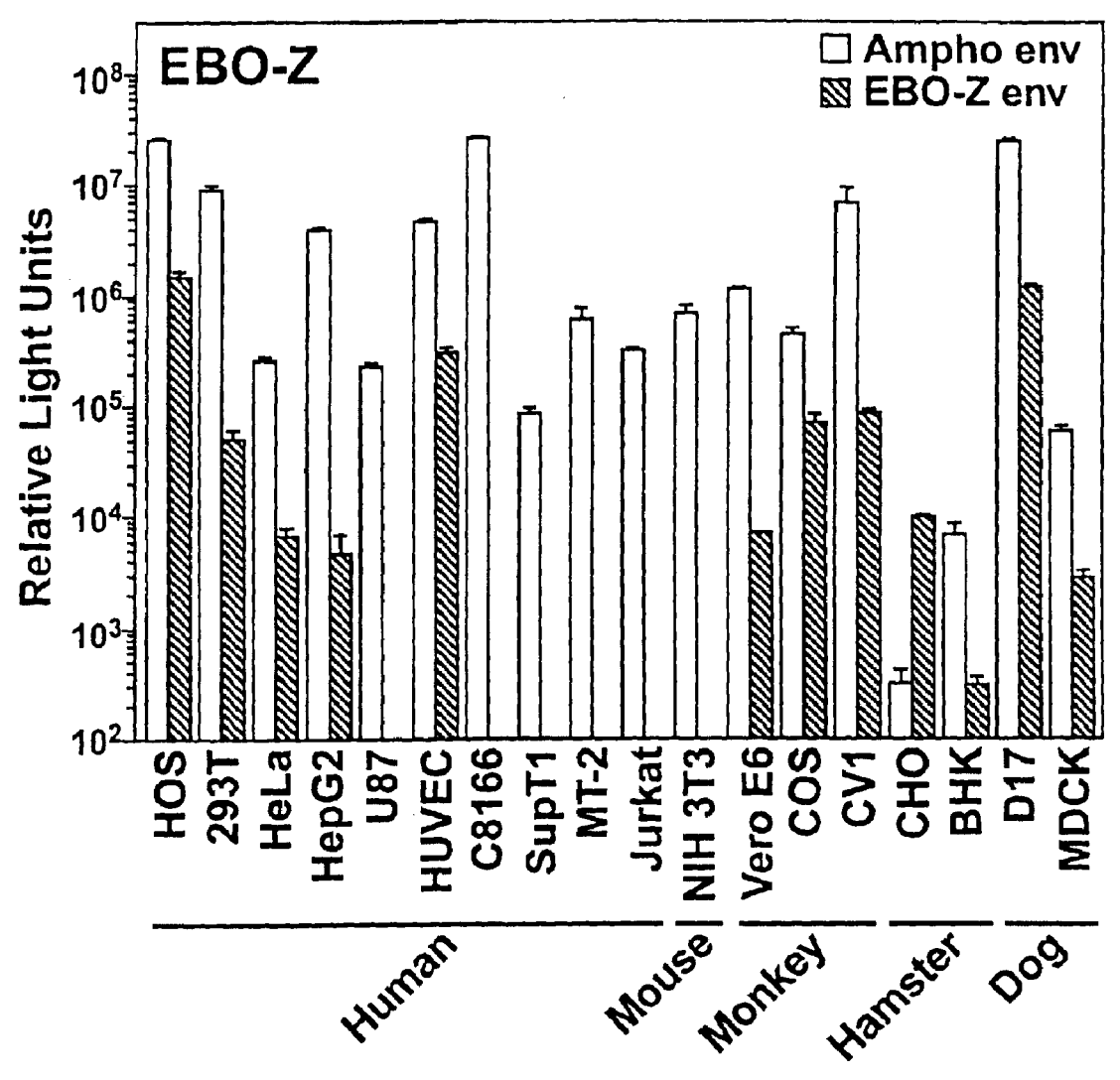
Figure 3:
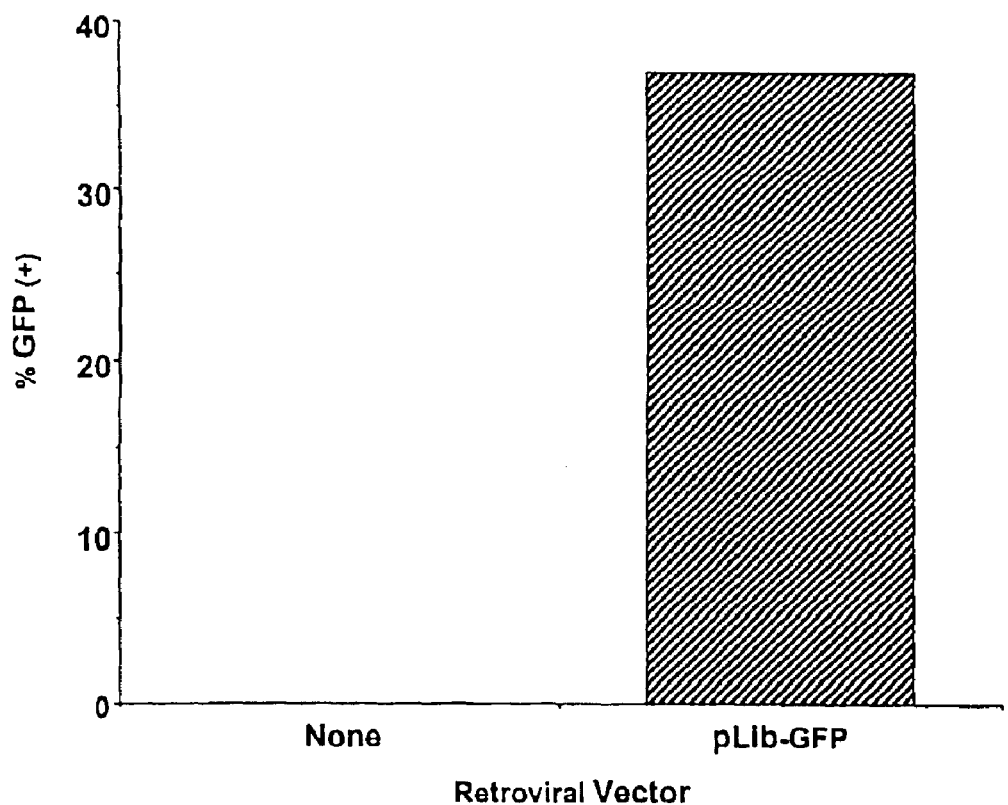
FIG. 3 provides a graphical representation of the efficiency of infection of Jurkat EctR with a retroviral cDNA library.

A cDNA encoding the Marburg (MBG) or Ebola-Zaire (EBZ) envelope glycoproteins (GP) was used to generate pseudotype viruses based on an envelope-negative clone of the human immunodeficiency virus type 1 (HIV-1) that had been engineered to contain a firefly luciferase gene (pNL4-3LucR-E-,provided by Dr. Nathaniel Landau, Salk Institute). The envelope cDNAs (pGEM-MBG, Xu et al., Nat. Med. 4(1):37–42, 1998; pGEM-EBO-Z, unpublished) were provided by Dr. Anthony Sanchez (Special Pathogens Branch, CDC). By quantitating infections using this indicator gene product, it was found that co-expressing the pNL4-3lucR-E and envelope construct led to production of infectious virions with the properties of the parental virus (Marburg or Ebola, respectively) (FIGS. 1A–1C) Numerous human and other cell lines were then screened for permissivity, and it was found that nearly all cells were permissive with the exception of several human T-cell lines (including Jurkat, MT-2,SupT1 and C8166; FIGS. 2A and 2B) For subsequent cloning experiments, a Jurkat derivative known as Jurkat-EctR (from Dr. Garry Nolan, Stanford Univ) was used. Jurkat-EctR cells were modified genetically by introduction of a cDNA library derived from HeLa cells. This library (purchased from Clontech, in the pLib Moloney-based vector) was introduced into Jurkat-EctR cells using a retroviral vector system that was optimized to achieve 30–40% transduction efficiency (FIG. 3). Cells that had been transduced with this library were "challenged" with a selectable MBG pseudotype virus. To prepare selectable pseudotype viruses, a modified pseudotype strategy was used in which the MBG GP was introduced into 293T cells by co-transfection along with an alternate HIV-1 proviral clone pHIV-blasti (provided by Dr. Richard Sutton Baylor College of Medicine) containing the blasticidin S deaminase gene from *Aspergillus terreus* rather than the luciferase gene. Pseudotype virions produced from these co-transfections were then used to "challenge" Jurkat-EctR cells. Two days following challenge, the cells were transferred into medium containing blasticidin S (ICN, 40 μg/ml) and monitored for viability (FIG. 4). In negative control samples (pseudovirions lacking envelope GP), all cells died within 8 days and no viable cells were recoverable over a 3-week interval. In positive control samples (pseudovirions containing envelope G-glycoprotein from vesicular stomatitis virus,VSV), numerous viable cells were evident. In the experimental samples (pseudovirions containing MBG GP), small numbers of viable cells were detected. These cells were expanded for additional study. In a key validation experiment, recovered cells were re-challenged with MBG GP pseudotype virus containing the luciferase gene, which confirmed that these cells were permissive for infection via the MBG envelope, unlike the parental cells (FIG. 5). Subsequently, these cells were subjected to limiting dilution to obtain individual cell clones.

In the next step, individual MBG-permissive clones were used to isolate genomic DNA by the "Easy DNA" method (Invitrogen) method. Genomic DNA was used as template for PCR-based amplification using oligonucleotide primers derived from the sequences flanking the cDNA inserts in the cDNA library. In experimental samples, but not control samples, specific DNA bands were amplified. These bands were extracted from agarose gels and used in conventional TA cloning steps using the pCR2.1 vector (Invitrogen). 12 Clones with independent inserts were recovered, and automated DNA sequencing was used to determine the sequences of these inserts. Based upon sequencing from two directions and assemblage of a contig based on overlapping sequences from these sequences runs, one insert (clone 4-1) showed perfect identity with the 3' two-thirds of known cDNAs recognized as encoding human FR-α.

To verify that this molecule serves as a receptor for MBG, a transfection experiment was performed in which this cDNA (subcloned into a mammalian expression vector, pCMV4Neo) was introduced transiently by electroporation into Jurkat-EctR cells. These cells were then challenged with pseudotype luciferase viruses and scored for luciferase signal as a marker of infection. Cells transfected with clone 4-1, but not empty vector, exhibited a significant luciferase signal (FIG. 6). Finally, we found that treatment of permissive cells with phospholipase C virtually abolished infection by MBG pseudotype, a finding that is consistent with the GPI (glycophosphatidylinositol) type of membrane linkage that is characteristic of folate receptor-alpha (FIG. 7). These findings confirm that the human FR-α as a receptor that mediates cellular entry by MBG.

Figure 8:
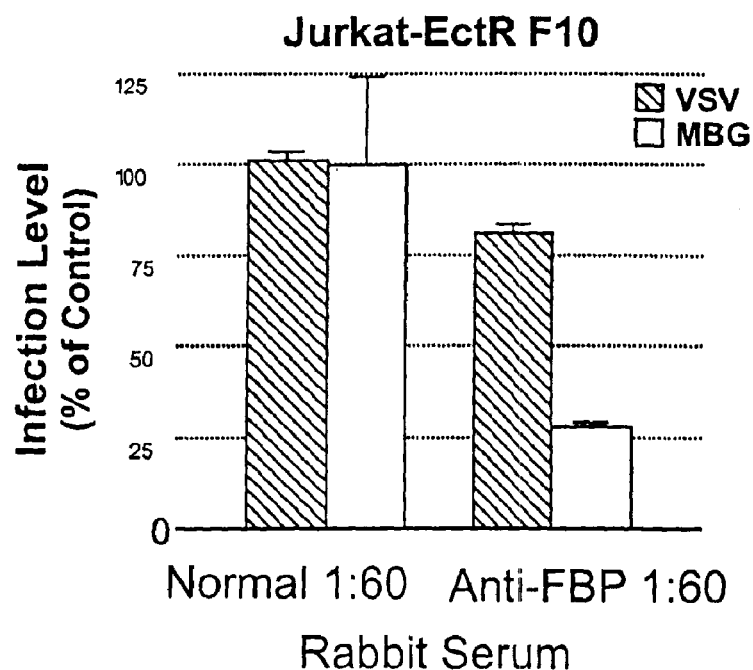
FIG. 8 provides the graphical results of an assay in which infection of a Jurkat EctR clone derived from the initial blasticidin selection following infection with Marburg psedutotype virus was completely inhibited by a commercially available rabbit polyclonal antiserum (from Biogenesis) raised against the human folate binding protein.
Figure 9:
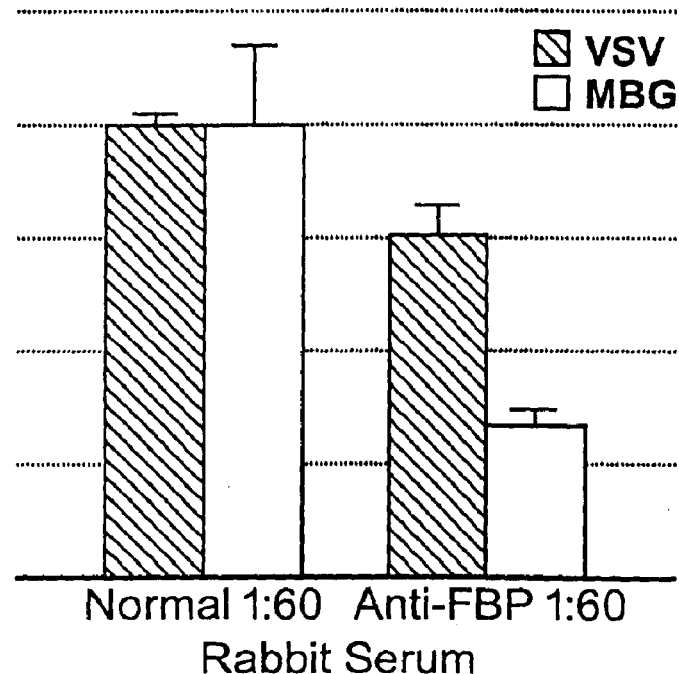
FIG. 9 provides the graphical results of an assay in which infection of Vero E6 cells by MBG lucerfase virus, but not by VSV luciferase virus, is inhibited in the presence of polyclonal rabbit anti-bovine folate binding protein, but not by normal rabbit serum.

Finally, pretreatments of JurkatEctR cells with a commercially available rabbit polyclonal antiserum raised against human folate binding protein (Biogenesis), a cleaved form of full-length FR-α, completely abolished infection by MBG pseudotype virus. (FIG. 8). To confirm these findings in a naturally injectable cell type, monkey Vero E6 cells, which are typically used to passage MBG virus in cell culture (Peters et al., (1996) Filoviridae: Marburg and Ebola Viruses. Fields Virology, Third Edition, eds. B N Fields, D M Knipe, P M Howley, et al. 1161–1176) and express significant levels of FR-α by Northern blot analysis, were challenged in the presence of anti-FBP. Entry by MBG was substantially inhibited by the anti-FBP antiserum (FIG. 9). Thus, similar inhibition of MBG entry was achieved on both genetically reconstituted human cells and untransduced monkey cells in the presence of polyclonal anti-FBP, indicating that FR-α is important in infection in different cell types and in different mammalian species.

Figure 10:
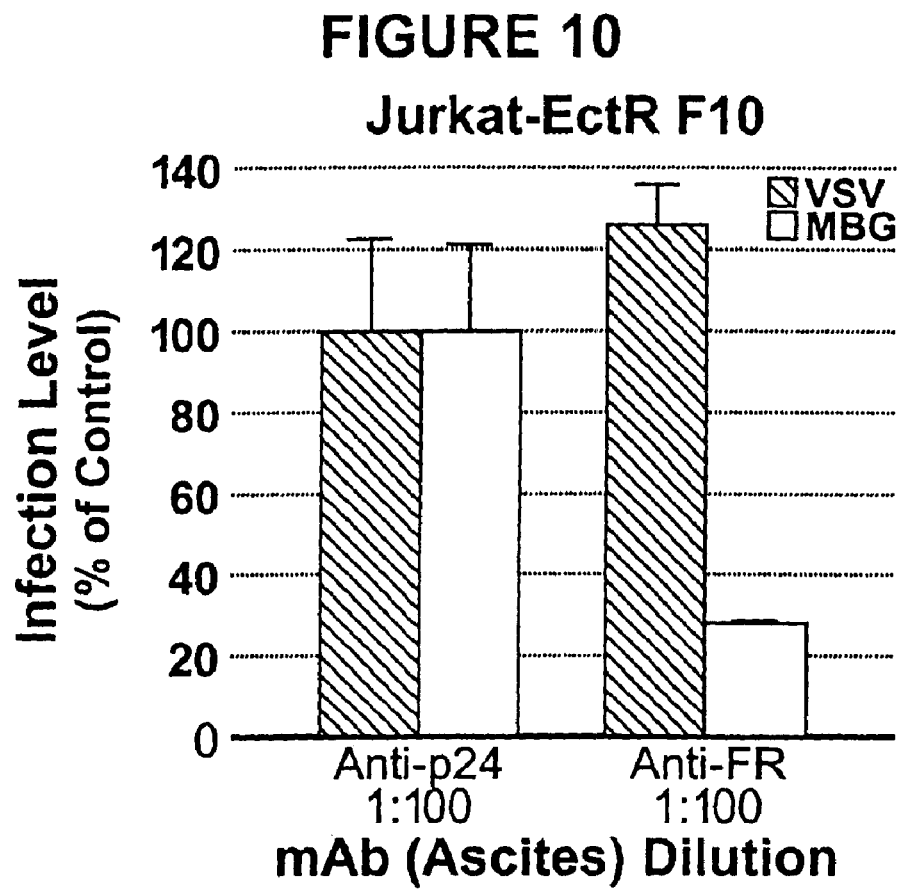
FIG. 10 provides the graphical results of an assay, showing that entry by MBG, but not VSV, luciferase virus into Jurkat-EctR F10 cells is specifically abrogated in the presence of mouse monoclonal anti-FR, compared to isotype control, antibody.

To determine if other antibodies that recognize relevant epitopes of FR-α similarly abrogated MBG entry, Jurkat-EctR F10 cells were challenged with pseudotype viruses in the presence of a monoclonal antibody preparation (No. 458) raised against human FR-α (FIG. 10). VSV entry was not inhibited in the presence of anti-FR-α compared with control ascites fluid containing isotype-matched monoclonal antibody recognizing an irrelevant HIV p24 antigen, while MBG infection was specifically and potently reduced by anti-FR-α. The specific inhibition of MBG entry by polyclonal or monoclonal antibodies raised separately against bovine FBP and human FR-α, respectively, further defines FR-α as a highly conserved mediator of MBG virus entry in multiple cell types and mammalian species.

Figure 11:
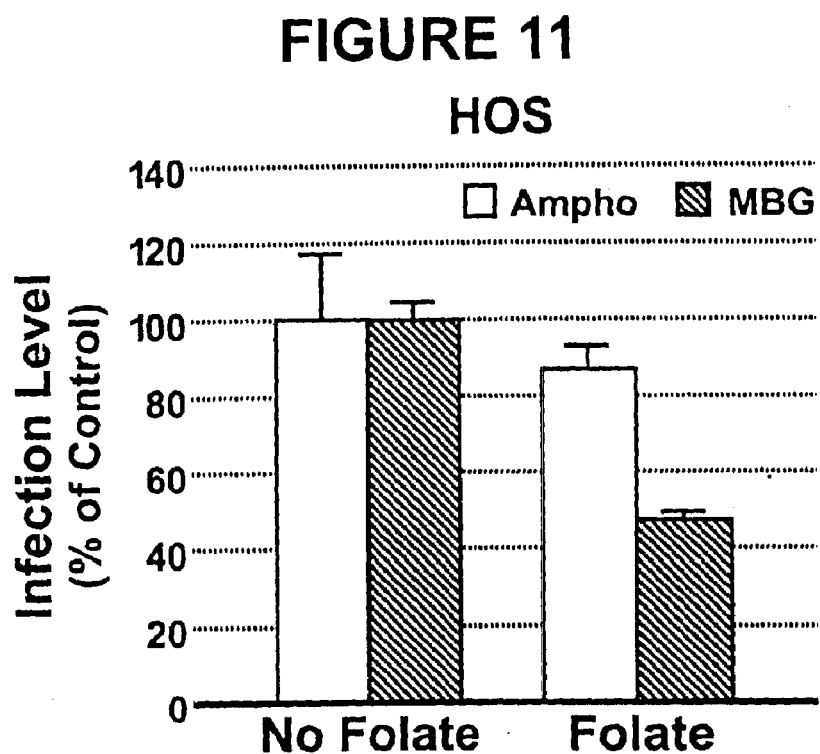
FIG. 11 provides the graphical results of an assay, showing that entry by MBG, but not Ampho, luciferase virus into human osteosarcoma cells is specifically inhibited by extracellular folic acid.

To test whether folic acid, a natural ligand of FR-α, is a specific inhibitor of MBG entry, pseudotype luciferase viruses were prepared in media containing neither fetal bovine serum (FBS) nor folic acid. Target cells (HOS) were then challenged with these virus preparations in the presence or absence of folic acid and a reduced form of folic acid, 5-methyltetrahydrofolic acid (10 $\mu$M), which is known to bind at high affinity to FR-α. Exposure to folic acid resulted in very slight alteration of entry by negative control Ampho luciferase pseudotypes. However, MBG virus entry was reduced by nearly 80% in the presence of folic acid (FIG. 11). This specific inhibition by folate compounds indicates that FR-α is important in MBG virus entry.

Figure 12:
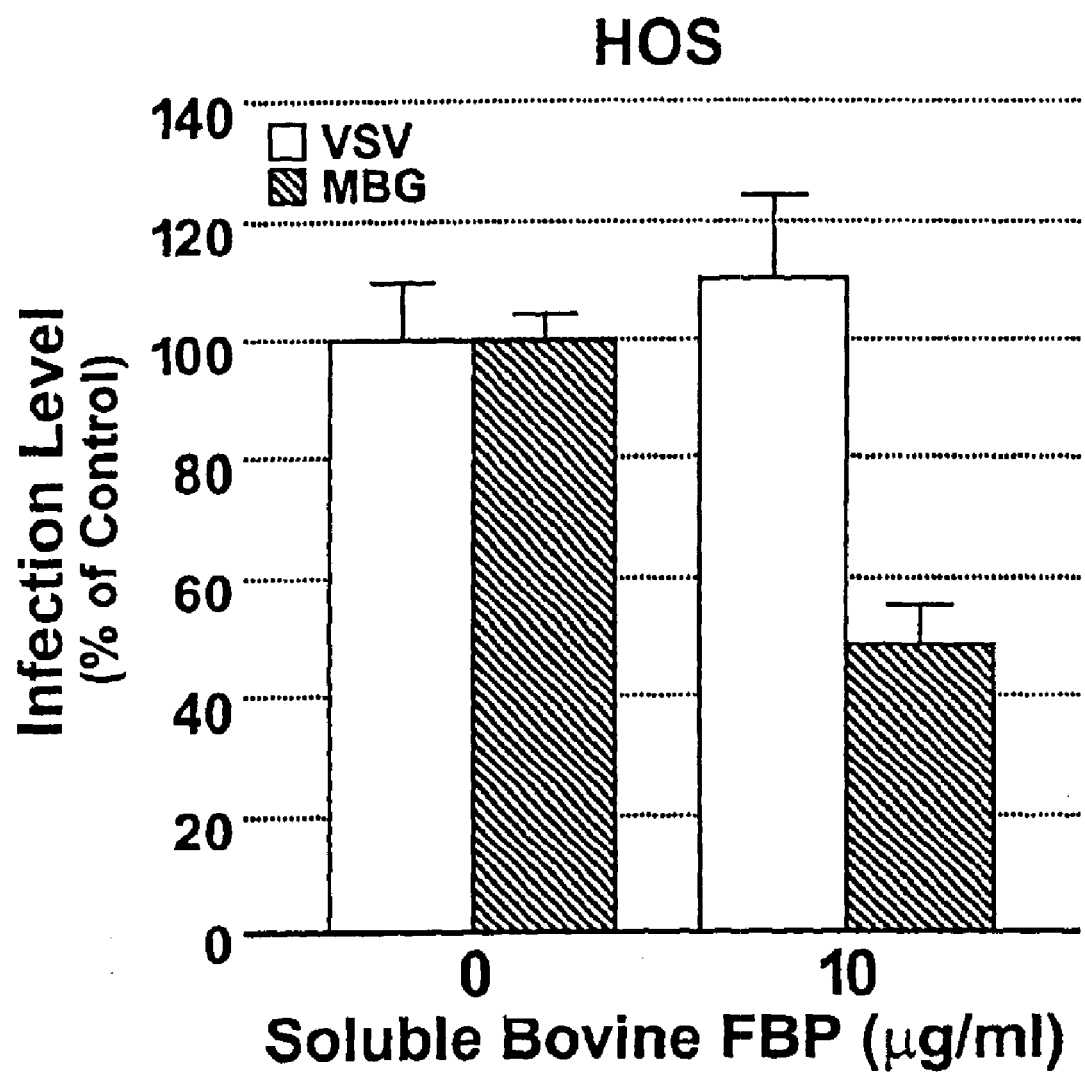
FIG. 12 provides the results of an assay showing that infection of HOS cells by MBG, but not VSV, luciferase virus specifically decreases in the presence of soluble bovine FBP.

Soluble FR-α inhibits MBG entry by interaction with virion GP. Another approach seeking to confirm a role for FR-α entailed using soluble FR-α to compete for the binding of MBG GP expressed on the virion envelope. Secreted FBP purified from bovine milk was pre-incubated with pseudotype luciferase viruses prepared in media lacking FBS or folic acid. HOS cells were then inoculated with these mixtures, and infection level was compared with that of uncomplexed virus. The results are shown in FIG. 12. VSV entry was not significantly altered in the presence of FBP while MBG entry was inhibited by more than 50% in the presence of FBP. Therefore, these results indicate that FR-α is an important factor that binds MBG virions at the cell surface.

To obtain direct evidence that MBG GP can bind FR-α, immunofluorescence microscopy was used to visualize FBP bound to the surface of cells expressing MBG GP. Since they express very low levels of FR-α (Weitman et al., (1992) Cancer Res. 52, 3396–3401; Orr and Kamen, (1995) Cancer Res. 55, 847–852), CHO-K1 cells were selected as target cells and were transfected with expression vectors encoding either MBG or Ampho GP. Two days following transfection, cells were incubated with bovine FBP and an anti-bovine FBP antibody that we found to be non-neutralizing for MBG entry. Samples were then fixed and stained with an anti-goat Ig fluorescein-conjugated secondary antibody in order to highlight selectively those cells with FBP bound to their surface. Transfected cells did not stain significantly when exposed to anti-FBP and secondary antibody in the absence of FBP, indicating that the low endogenous levels of FR-α on CHO-K1 cells cause little background staining. Additionally, cells transfected with Ampho GP exhibited only a low level of background staining in the presence of FBP. In contrast, cells expressing MBG GP and incubated with FBP displayed a ring-like cell surface staining of significantly higher intensity. The significant and specific staining of cells expressing MBG GP by FBP provides direct evidence that MBG GP can bind FBP, which further substantiates a role for FR-α in entry by MBG.

Figure 13:
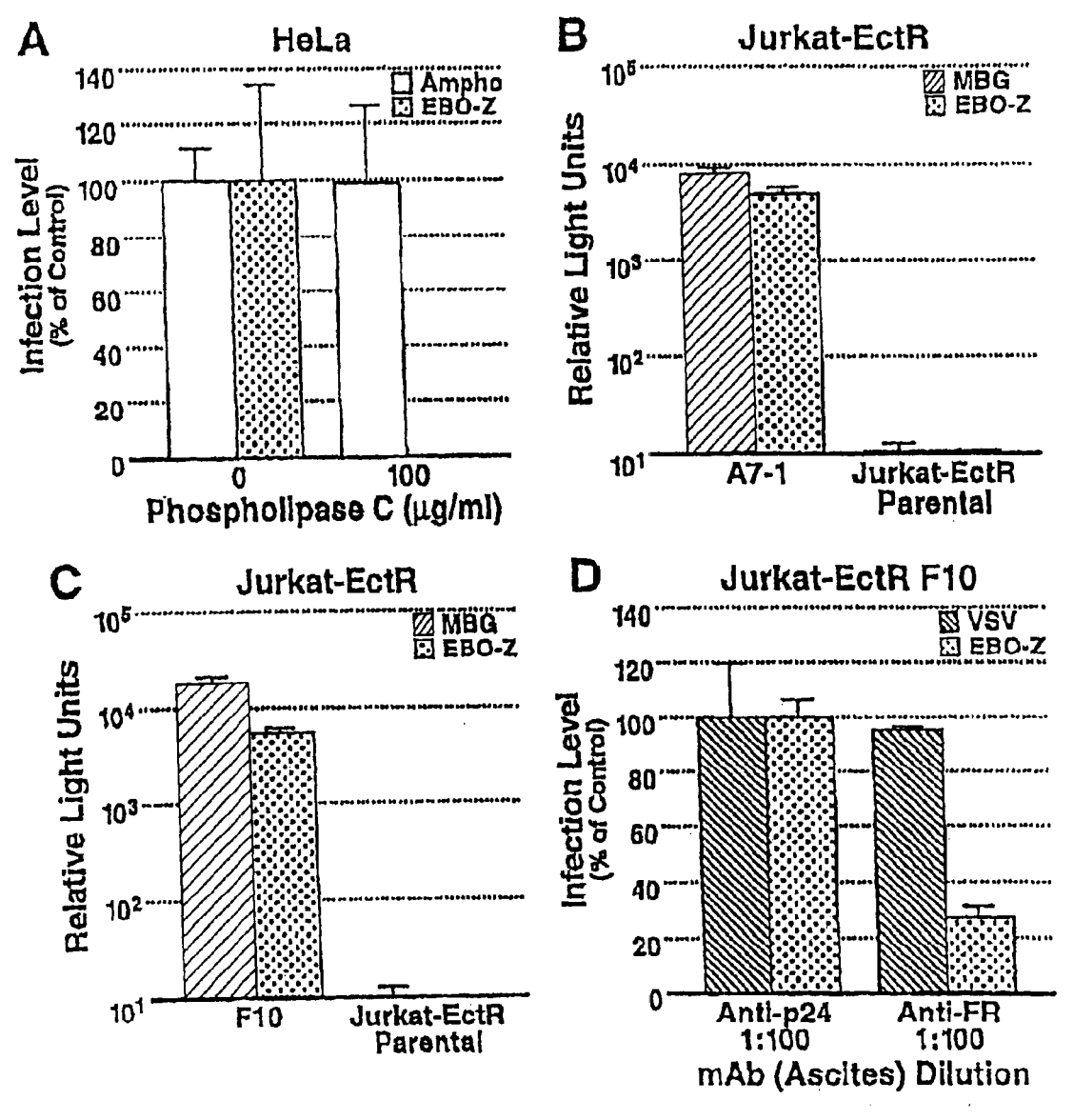

MBG GP and EBO-Z GP share common target cell factors for mediating virus entry. We examined the mechanisms of target cell entry utilized by EBO. As with MBG, cellular entry controlled by the EBO-Z GP was pH dependent (Wool-Lewis and Bates, (1998) J. Virol. 72, 3155–3160; Chan et al., (2000) J. Virol. 74, 4933–4937). Pre-treatment of HeLa cells with phospholipase C abolished entry by EBO-Z pseudotype virus, but not by Ampho virus (FIG. 13A). These results raised the possibility that entry by EBO-Z is also mediated by a GPI-linked protein.

The genetic complementation protocol described earlier was adapted for use in identifying host proteins that mediate entry by EBO-Z virus. Previous studies had demonstrated that HeLa cells, but not Jurkat cells, are permissive to entry mediated by EBO-Z GP (Chan et al., (2000) J. Virol. 74 4933–4937). Therefore, after delivery of the retroviral HeLa cDNA library into Jurkat-EctR cells, transduced Jurkat-EctR cells were challenged with pseudotype virus packaged by EBO-Z GP with the pHIV-blasti backbone (EBO-Z-blasti), and then selected in blasticidin S. Only the library-transduced cultures that had been challenged by EBO-Z-blasti virus yielded viable cells that survived selection. Subsequently, individual cell clones were expanded by limiting dilution and re-challenged with pseudotype luciferase viruses. For example, cell clone A7-1, which had been selected for EBO-Z permissivity, was indeed injectable by EBO-Z luciferase virus while parental cells were not (FIG. 13B). Importantly, A7-1 was also found to be permissive for entry by MBG luciferase virus. Therefore, by genetically complementing the deficiency of permissivity to EBO-Z virus entry, MBG entry was concurrently restored. Similarly, the Jurkat-EctR F10 cell clone that had been selected for MBG permissivity was injectable by MBG and EBO-Z luciferase viruses (FIG. 13C). Thus, in two independent iterations of library transduction and virus challenge followed by selection, one approach utilizing MBG pseudotypes and the other utilizing EBO-Z pseudotypes, recovered cells were found to be permissive for both MBG and EBO-Z infection. These results suggest that MBG and EBO-Z viruses depend on at least one common factor in target cells to gain entry.

FR-α mediates entry by EBO-Z virus. To identify the cDNA insert in A7-1 cells responsible for reconstituting permissivity of MBG and EBO-Z infection, RT-PCR was performed using mRNA isolated from A7-1 cells and primers recognizing the library retroviral sequences flanking the insert. A cDNA insert carrying 100% identity with the full-length FR-α was isolated, including the natural methionine initiation codon, suggesting that FR-α mediates infection by EBO-Z as well as by MBG virus.

To investigate the importance of FR-α for entry by EBO-Z virus, Jurkat-EctR F10 cells were challenged with pseudotype luciferase viruses in the presence of monoclonal anti-FR-α antibody or isotype-matched control antibody. While VSV control pseudotype infection levels were unaffected, infection by EBO-Z pseudotype virus decreased significantly in the presence of the anti-FR-α preparation (FIG. 13D). This result provides biochemical evidence that FR-α is a mediator of EBO-Z entry.

Figure 14:
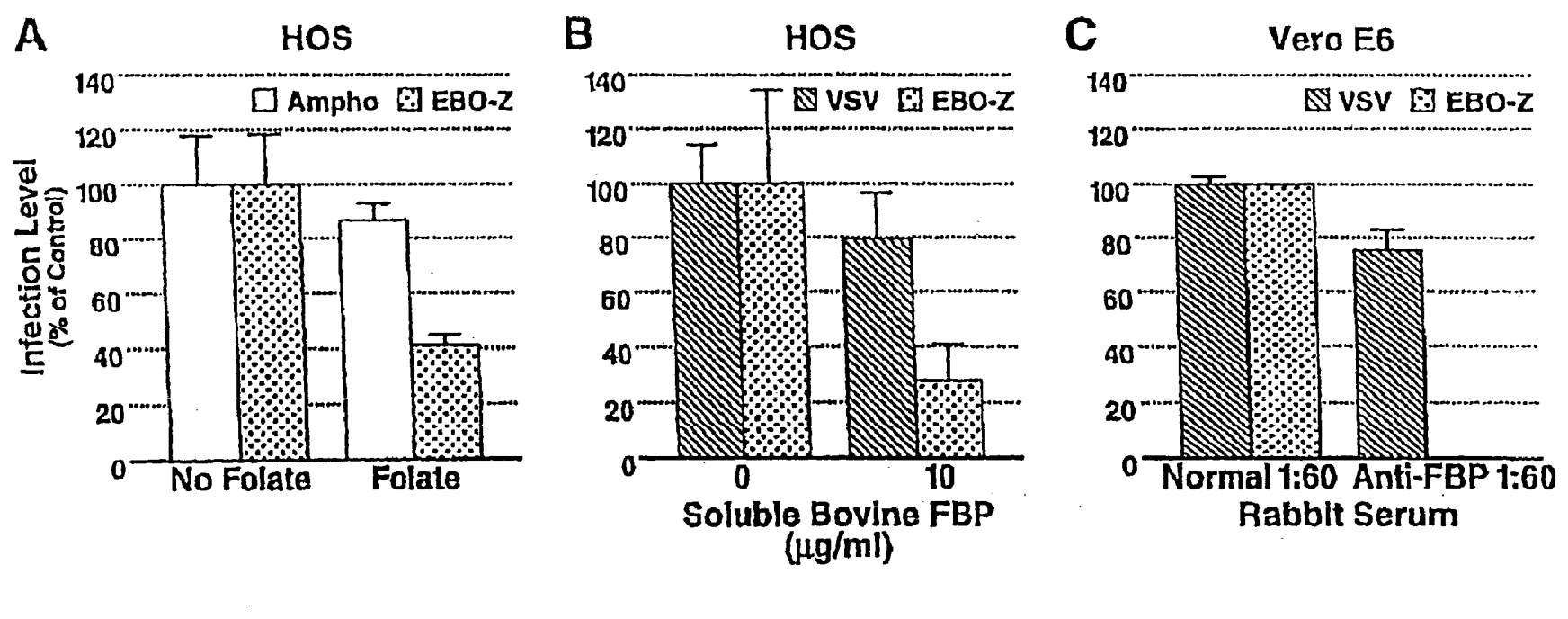

Further strategies to identify FR-α as a mediator of EBO-Z infection included inoculating HOS cells with luciferase viruses in the presence or absence of folic acid. While infection by Ampho virus did not significantly decrease in the presence of folic acid, entry by EBO-Z virus was inhibited significantly (FIG. 14A). In addition, virus challenge of HOS cells in the presence of FBP caused no significant decrease in entry by VSV pseudotypes but a substantial inhibition of EBO-Z infection (FIG. 14B). Therefore, mirroring the inhibition profiles observed for MBG virus, EBO-Z pseudotype virus entry was specifically abrogated in the presence of agents expected to disrupt interactions between virion GP and FR-α.

Finally, to assess the role of FR-α in mediating EBO-Z entry in naturally permissive cell types routinely used for study of filovirus infection (Peters et al., (1996) Filoviridae: Marburg and Ebola Viruses. Fields Virology, Third Edition, eds. B N Fields, D M Knipe, P M Howley, et al. 1161–1176.), Vero E6 cells were challenged with EBO-Z luciferase virus in the presence of either polyclonal rabbit anti-bovine FBP antibody or normal rabbit sera. VSV entry decreased marginally in the presence of anti-FR-α, while EBO-Z entry was completely abrogated in the presence of the anti-FR-α preparation (FIG. 14C). Therefore, as with MBG infection, EBO-Z entry was specifically inhibited in the presence of monoclonal or polyclonal anti-FR-α antibodies, folic acid, or soluble FBP. Considered together with the recovery of independent cDNA inserts encoding FR-α from separate library transductions challenged with either MBG or EBO-Z-blasti viruses, we conclude that FR-α is a cofactor for cellular entry by either MBG or EBO-Z virus.

The above results and discussion indicate that the subject invention provides important new means of modulating and even inhibiting filovirus entry into permissive cells. As such, the subject invention provides new means of treating the devastating illness mediated by filoviruses. Therefore, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of a identifying a cell surface receptor used by a filovirus for entry into a cell, said method comprising:
    (a) transfecting a population of cells of a cell line that is non-permissive for entry of said filovirus with nucleic acid obtained from a cell line permissive for entry of said filovirus, wherein the nucleic acid is genomic DNA or cDNA;
    (b) identifying at least one cell from said transfected cell population which is permissive for entry of said filovirus; and
    (c) identifying at least one permissive cell-derived nucleic acid in the genome of said transfected permissive cell, wherein the at least one permissive-cell-derived nucleic acid encodes a cell surface receptor used by said filovirus for entry into the cell.

2. The method of claim 1, wherein the filovirus is a Marburg virus.

3. The method of claim 1, wherein the filovirus is an Ebola virus.

4. The method of claim 1, wherein a cell line that is permissive for entry of a filovirus is identified by contacting the cell with a viral particle, and determining entry of the filovirus into the cell.

5. The method of claim 4, wherein entry of the filovirus is determined by detecting expression of filovirus proteins on the cell surface.

6. The method of claim 1, wherein a cell line that is permissive for entry of a filovirus is identified by contacting the cell with pseudotyped virus that comprises a selectable marker and a glycoprotein of the filovirus.

7. The method of claim 1, wherein the population of cells of a cell line that is non-permissive for entry of said filovirus are transfected with cDNA obtained from a cell line permissive for entry of said filovirus, wherein the cDNA is flanked by a nucleic acid of a retrovirus, and wherein the at least one permissive cell-derived cDNA is identified by using a polymerase chain reaction with primers that hybridize to the retrovirus sequences.

* * * * *